United States Patent [19]

Wesley et al.

[11] Patent Number: 6,015,663
[45] Date of Patent: Jan. 18, 2000

[54] RESTRICTION ENZYME SCREEN FOR DIFFERENTIATING PORCINE REPRODUCTIVE AND RESPIRATORY SYNDROME VIRUS STRAINS

[75] Inventors: Ronald D. Wesley; Deborah F. Clouser; William L. Mengeling, all of Ames, Iowa; Vladimir G. Andreyev, Vladimir, Russian Federation; Ann C. Vorwald, Ames; Kelly M. Lager, Nevada, both of Iowa

[73] Assignee: The United States of America as represented by the Secretary of Agriculture, Washington, D.C.

[21] Appl. No.: 08/609,334

[22] Filed: Mar. 1, 1996

[51] Int. Cl.[7] .............................. C12Q 1/70; C12Q 1/68
[52] U.S. Cl. .................. 435/5; 435/6; 435/91.2; 536/23.72; 536/24.33
[58] Field of Search ...................... 435/235.1, 5, 69.1, 435/91.1, 91.33, 91.2, 6; 536/23.1, 23.72, 24.3, 24.33

[56] References Cited

U.S. PATENT DOCUMENTS 5,587,164  12/1996  Sanderson et al. .................. 424/218.1

FOREIGN PATENT DOCUMENTS 0595436  4/1994  European Pat. Off. .

OTHER PUBLICATIONS

Mengeling, William L., et al., "Temporal characterization of transplacental infection of porcine fetuses with porcine reproductive and respiratory syndrome virus", *Am. J. Vet. Res.*, vol. 55, No. 10, Oct. 1994, pp. 1391–1398.

Mengeling, William L., et al., "Diagnosis of porcine reproductive and respiratory syndrome", *J. Vet. Diagn. Invest.*, vol. 7, pp. 3–16, 1995.

Meng et al. "Molecular cloning and nucleotide sequencing of the 3'–terminal genomic RNA of the porcine reproductive and respiratory syndrome virus". J. General Virology. vol. 75:1795–1801, 1994.

Vilgalys et al. "Rapid Genetic Identification and Mapping of Enzymatically Amplified ribosomal DNA from Several Cryptococcus Species". Journal of Bacteriology. vol. 172, No. 8:4238–4246, Aug. 1990.

Jayarao et al. "Differentiation of *Streptococcus uberis* from *Streptococcus parauberis* by Polymerase Chain Reaction and Restriction Fragment Length polymorphism Analysis of 16S Ribosomal DNA". Journal of Clinical Microbiology. vol. 29, No. 12:2774–2778, Dec. 1991.

Marconi et al. "Phylogenetic Analysis of the Genus Borrelia: a Comparison of North American and European Isolates of *Borrelia burgdorferi*". Journal of Bacteriology. vol. 174, No. 1:241–244, Jan. 1992.

Meng, Xiang–Jin, et al., "Sequence comparison of open reading frames 2 to 5 of low and high virulence United States isolates of porcine reproductive and respiratory syndrome virus", *Journal of General Virology*, 1995, 76, pp. 3181–3188.

Mardassi, H., et al., "Molecular analysis of the ORFs 3 to 7 of porcine reproductive and respiratory syndrome virus, Québec reference strain", *Arch. Virol.*, 1995, 140, pp. 1405–1418.

*Primary Examiner*—Donna C. Wortman
*Attorney, Agent, or Firm*—M. Howard Silverstein; Curtis P. Ribando; John D. Fado

[57] ABSTRACT

A test based on restriction enzyme analysis identifies and differentiates strains of porcine reproductive and respiratory syndrome virus (PRRSV). Amplified cDNA from the ORF 5 region of the viral genome has been targeted for identification of unique restriction sites that allow for the differentiation of the vaccine strain from field strains, and for differentiation of field strains from each other through the use of selected restriction enzymes. This assay is useful for both clinical diagnosis of PRRSV field strains in vaccinated pigs as well as for epidemiological studies in the evaluation of the source and transmission of PRRS field viruses.

9 Claims, 17 Drawing Sheets

| | | |
|---|---|---|
| RESPPRRS | ATGTTGGAGA AATGCTTGAC CGCGGGCTGT TGCTCGCAAT TGCTTTCTTT | 50 |
| VR2332 | ATGTTGGAGA AATGCTTGAC CGCGGGCTGT TGCTCGCGAT TGCTTTCTTT | 50 |
| Consensus | ATGTTGGAGA AATGCTTGAC CGCGGGCTGT TGCTCGCRAT TGCTTTCTTT | 50 |
| RESPPRRS | GTGGTGTATC GTGCCGTTCT GTTTTGCTGT GCTCGCCAAC GCCAGCAACG | 100 |
| VR2332 | GTGGTGTATC GTGCCGTTCT GTTTTGCTGT GCTCGCCAAC GCCAGCAACG | 100 |
| Consensus | GTGGTGTATC GTGCCGTTCT GTTTTGCTGT GCTCGCCAAC GCCAGCAACG | 100 |
| RESPPRRS | ACAGCAGCTC CCATCTACAG CTGATTTACA ACTTGACGCT ATGTGAGCTG | 150 |
| VR2332 | ACAGCAGCTC CCATCTACAG CTGATTTACA ACTTGACGCT ATGTGAGCTG | 150 |
| Consensus | ACAGCAGCTC CCATCTACAG CTGATTTACA ACTTGACGCT ATGTGAGCTG | 150 |
| RESPPRRS | AATGGCACAG ATTGGCTAGC TAACAAATTT GATTGGGCAG TGGAGAGTTT | 200 |
| VR2332 | AATGGCACAG ATTGGCTAGC TAACAAATTT GATTGGGCAG TGGAGAGTTT | 200 |
| Consensus | AATGGCACAG ATTGGCTAGC TAACAAATTT GATTGGGCAG TGGAGAGTTT | 200 |
| RESPPRRS | TGTCATCTTT CCCGTTTTGA CTCACATTGT CTCCTATGGT GCCCTCACTA | 250 |
| VR2332 | TGTCATCTTT CCCGTTTTGA CTCACATTGT CTCCTATGGT GCCCTCACTA | 250 |
| Consensus | TGTCATCTTT CCCGTTTTGA CTCACATTGT CTCCTATGGT GCCCTCACTA | 250 |
| RESPPRRS | CCAGCCATTT CCTTGACACA GTCGCTTTAG TCACTGTGTC TACCGCCGGG | 300 |
| VR2332 | CCAGCCATTT CCTTGACACA GTCGCTTTAG TCACTGTGTC TACCGCCGGG | 300 |
| Consensus | CCAGCCATTT CCTTGACACA GTCGCTTTAG TCACTGTGTC TACCGCCGGG | 300 |

FIG. 1A

| | | | | |
|---|---|---|---|---|
| RESPPRRS | TTTGTTCACG | GGCGGTATGT | CCTAAGTAGC | ATCTACGCCG | TCTGTGCCCT | 350 |
| VR2332 | TTTGTTCACG | GGCGGTATGT | CCTAAGTAGC | ATCTACGCCG | TCTGTGCCCT | 350 |
| Consensus | TTTGTTCACG | GGCGGTATGT | CCTAAGTAGC | ATCTACGCCG | TCTGTGCCCT | 350 |
| | | | | |
| RESPPRRS | GGCTGCGGTTG | ACTTGCTTG | TCATTAGTT | TGCAAAGAAT | TGCATGTCCT | 400 |
| VR2332 | GGCTGCGGTTG | ACTTGCTTG | TCATTAGTT | TGCAAAGAAT | TGCATGTCCT | 400 |
| Consensus | GGCCGCGGTTG | ACTTGCTTG | TCATTAGTT | TGCAAAGAAT | TGCATGTCCT | 400 |
| | | | | |
| RESPPRRS | GGGCCTACGC | GTGTACCAGA | TATACCAACT | TTCTTCTCTGA | CACTAAGGGC | 450 |
| VR2332 | GGGCCTACGC | GTGTACCAGA | TATACCAACT | TTCTTCTCTGA | CACTAAGGGC | 450 |
| Consensus | GGGCCTACGC | GTGTACCAGA | TATACCAACT | TTCTTCTCTGA | CACTAAGGGC | 450 |
| | | | | |
| RESPPRRS | CGACTCTATC | GTTGGCGGTC | GCCTGTCATC | ATAGAGAAAA | GGGCAAAGT | 500 |
| VR2332 | AGACTCTATC | GTTGGCGGTC | GCCTGTCATC | ATAGAGAAAA | GGGCAAAGT | 500 |
| Consensus | RGACTCTATC | GTTGGCGGTC | GCCTGTCATC | ATAGAGAAAA | GGGCAAAGT | 500 |
| | | | | |
| RESPPRRS | TGAGGTCGAA | GGTCATCTGA | TCGACCTCAA | AAGAGTTGTG | CTTGATGGTT | 550 |
| VR2332 | TGAGGTCGAA | GGTCATCTGA | TCGACCTCAA | AAGAGTTGTG | CTTGATGGTT | 550 |
| Consensus | TGAGGTCGAA | GGTCATCTGA | TCGACCTCAA | AAGAGTTGTG | CTTGATGGTT | 550 |
| | | | | |
| RESPPRRS | CCGTGGCAAC | CCCTATAACC | AGAGTTTCAG | CGGAACAATG | GGGTCGTCCT | 600 |
| VR2332 | CCGTGGCAAC | CCCTATAACC | AGAGTTTCAG | CGGAACAATG | GGGTCGTCCT | 600 |
| Consensus | CCGTGGCAAC | CCCTATAACC | AGAGTTTCAG | CGGAACAATG | GGGTCGTCCT | 600 |

FIG. 1B

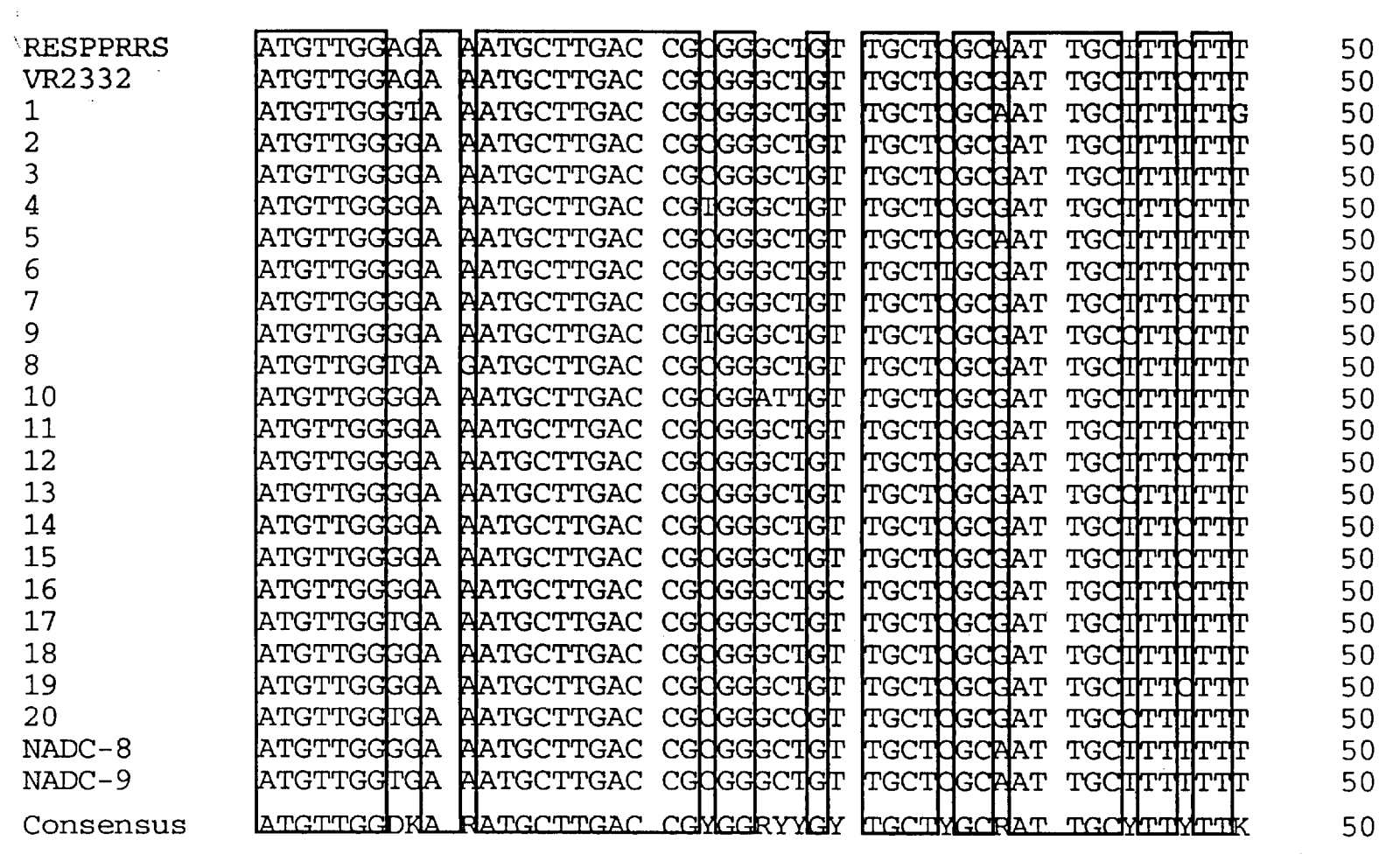

| | | | | | |
|---|---|---|---|---|---|
| RESPPRRS VR2332 | ATGTTGGAGA | AATGCTT

FIG. 2B

| | | | | | |
|---|---|---|---|---|---|
| RESPPPRRS | ACAGCAGCTC | CGATCTACAG | CTGATTTACA | ACTTGACGCT | ATGTGAGCTG 150 |
| VR2332 | ACAGCAGCTC | CGATCTACAG | CTGATTTACA | ACTTGACGCT | ATGTGAGCTG 150 |
| 1 | ACAGCAGCTC | AAATTTACAG | CTGATTTACA | ACTTGACGCT | ATGTGAGCTG 150 |
| 2 | ACAGCAGCTC | CGAATTTACAG | CTGATTTACA | ACTTGACGCT | ATGTGAGCTG 150 |
| 3 | ACAGCAGCTC | TCAATTTACAG | CTGATTTACA | ACTTGACGCT | ATGTGAGCTG 150 |
| 4 | ACAGCAGCTC | TCATCTGCAA | TTGATTTACA | ACTTGACGCT | ATGTGAGCTG 150 |
| 5 | ACAGCAGCTC | AAATTTACAG | CTGATTTACA | ACTTGACGCT | ATGTGAGCTG 150 |
| 6 | CCAGCAGCTC | CCATTTACAG | CCAGTTTACA | ACTTGACGCT | ATGTGAGCTG 150 |
| 7 | ACAGCAGCTC | TCATTTTCAG | TTGATTTACA | ACTTGACGCT | ATGTGAGCTG 150 |
|

| | | | | | | | | | | |
|---|---|---|---|---|---|---|---|---|---|---|
| RESPPRRS | GGCGCTACGC | GTGTACCAGA | TATACCAACT | TTCTTCTGGA | CACTAAGGGC | 450 |
| VR2332 | GGCGCTACGC | GTGTACCAGA | TATACCAACT | TTCTTCTGGA | CACTAAGGGC | 450 |
| 1 | GGCGCTACTC | ATGTACCAGA | TATACCAACT | TTCTTCTGGA | CACTAAGGGC | 450 |
| 2 | GGCGCTATTC | ATGTACCAGA | TATACCAACT | TTCTTCTGGA | CACTAAGGGC | 450 |
| 3 | GGCGCTACTC | ATGTACCAGA | TATACCAACT | TTCTTCTGGA | CACTAAGGGC | 450 |
| 4 | GGCGCTATTC | ATGTACCAGA | TATACCAACT | TTCTTCTGGA | TACTAAGGGC | 450 |
| 5 | GGCGCTACTC | ATGTACCAGA | TATACCAACT | TTCTTCTGGA | TACTAAGGGC | 450 |
| 6 | GGCGCTACTC | ATGTACCAGA | TATACCAACT | TTCTTCTGGA | CACCAAGGGC | 450 |
| 7 | GGCGCTACTC | ATGTACCAGA | TATACCAACT | TTCTTCTGGA | TACTAAGGGC | 450 |
| 8 | GGCGCTACTC | ATGTACCAGA | TATACCAACT | TTCTTCTAGA | CACTAAGGGC | 450 |
| 9 | GGCGCTACTC | ATGTACCAGA | TATACCAACT | TTCTTCTGGA | CACTAAGGGC | 450 |
| 10 | GGCGCTACTC | ATGTACCAGA | TATACCAACT | TCCTTCTGGA | CACTAAGGGC | 450 |
| 11 | GGCGCTACTC | ATGTACCAGA | TATACCAACT | TTCTTCTGGA | CACTAAGGGC | 450 |
| 12 | GGCGCTACTC | ATGTACCAGA | TATACCAACT | TTCTTCTGGA | CACCAAGGGC | 450 |
| 13 | GGCGCTACTC | ATGTACCAGA | TATACCAACT | TTCTTCTGGA | CACTAAGGGC | 450 |
| 14 | GGCGCTACTC | TTGTACCAGA | TATACCAACT | TTCTTCTGGA | CACTAAGGGC | 450 |
| 15 | GGCGCTACTC | ATGTACCAGA | TATACCAACT | TTCTTCTGGA | CACCAAGGGC | 450 |
| 16 | GGCGCTACTC | ATGTACCAGA | TATACCAACT | TCCTTCTGGA | CACTAAGGGC | 450 |
| 17 | GGCGCTACTC | ATGTACCAGA | TATACCAACT | TCCTTCTGGA | CACTAAGGGC | 450 |
| 18 | GGCGCTACTC | ATGTACCAGA | TATACCAACT | TCCTTCTGGA | CACTAAGGGC | 450 |
| 19 | GGCGCTACTC | ATGTACCAGA | TATACCAACT | TCCTTCTGGA | CACCAAGGGC | 450 |
| 20 | GGCGCTACTC | ATGTACCAGA | TATACCAACT | TCCTTCTGGA | CACTAAGGGC | 450 |
| NADC-8 | GGCGCTACTC | ATGTACCAGA | TATACCAACT | TTCTTCTGGA | CACCAAGGGC | 450 |
| NADC-9 | GGCGCTACTC | ATGTACCAGA | CATACCAACT | TTCTTCTGGA | CACTAAGGGC | 450 |
| Consensus | GGCGCTAYKC | DTGYACYAGA | YATACYAACT | TYCTYCTRGA | YACYAAGGGC | 450 |

| | | |
|---|---|---|
| RESPPRRS | TAG | 603 |
| VR2332 | TAG | 603 |
| 1 | TAG | 603 |
| 2 | TAG | 603 |
| 3 | TAG | 603 |
| 4 | TAG | 603 |
| 5 | TAG | 603 |
| 6 | TAG | 603 |
| 7 | TAG | 603 |
| 9 | TAG | 603 |
| 8 | TAG | 603 |
| 10 | TAG | 603 |
| 11 | TAG | 603 |
| 12 | TAG | 603 |
| 13 | TAG | 603 |
| 14 | TAG | 603 |
| 15 | TAG | 603 |
| 16 | TAG | 603 |
| 17 | TAG | 603 |
| 18 | TAG | 603 |
| 19 | TAG | 603 |
| 20 | TAG | 603 |
| NADC-8 | TAG | 603 |
| NADC-9 | TAG | 603 |
| Consensus | TAG | 603 |

RESTRICTION ENZYME SCREEN FOR DIFFERENTIATING PORCINE REPRODUCTIVE AND RESPIRATORY SYNDROME VIRUS STRAINS

BACKGROUND OF THE INVENTION

1. Field of the Invention

This invention relates to a differential test for distinguishing strains of Porcine Reproductive and Respiratory Syndrome Virus (PRRSV) from one another and for differentiating field stains from the currently used vaccine strain.

Porcine reproductive and respiratory syndrome (PRRS) was first reported in North America in 1987 (Keffaber, 1989) and emerged in Europe in late 1990 (Wensvoort et al., 1991). Recently, PRRS has gained world-wide attention because of its economic impact on the swine industry. The disease is characterized by reproductive failure in pregnant sows and respiratory problems in pigs of all ages (Loula, 1991). The causative agent of PRRS is a small (50–60 nm) positive-stranded RNA enveloped virus. The genome is a polyadenylated RNA molecule of about 15 kb and contains eight open reading frames (ORFs). Viral proteins are expressed by six subgenomic mRNAs which are transcribed from the negative strand using a body sequence derived from the 5' end of the viral genome (Meulenberg et al., 1995). The virus replicase is most likely encoded by ORFs 1a/1b by a −1 frameshift (Conzelmann et al., 1993). Open reading frames 2 to 4 encode for putative structural proteins (Van Nieuwstadt, 1995). ORF 5 encodes for a envelope (E) glycoprotein of approximately 25 kDa. A non-glycosylated membrane (M) protein of 18 kDa is encoded by ORF 6 and the nucleocapsid (N) protein of 15 kDa is encoded by ORF 7 (Meulenberg et al., 1995; Conzelmann et al., 1993).

Morphologically and morphogenetically, PRRSV resembles equine arteritis virus (EAV), lactate dehydrogenase-elevating virus (LDV), and simian hemorrhagic fever virus (SHFV) (Conzelmann et al., 1993; Meulenberg et al., 1993; Plagemann and Moennig, 1991; Snijder and Spaan, 1995). As a result of common features shared by these viruses, they have been tentatively grouped into a new virus family, Arteriviridae (Conzelmann et al., 1993; Meulenberg et al., 1993, Plagemann and Moennig, 1992).

2. Description of the Prior Art

Although the clinical features of PRRS in the United States and in Europe appear similar, several recent studies have indicated phenotypic, antigenic, and genetic differences exist among PRRSV isolates (Bautista et al., 1993; Meng et al., 1994; Wensvoort et al., 1992). The amino acid sequences of ORF 2 through ORF 7 of North American isolates share only 55–79% homology with those of European descent (Meulenberg et al., 1995). It is believed that the glycosylated structural envelope protein E, encoded by ORF 5, is partially responsible for these serological variations among isolates of PRRSV (Meulenberg et al., 1995). Protein E is the counterpart of $G_L$ of EAV (de Vries et al., 1992) and VP-3 of LDV (Gogeny et al., 1993). Both ($G_L$ and E) proteins contain a large internal hydrophobic region which has been thought to anchor these proteins in the membrane (Meulenberg et al., 1995). The existence of neutralizing epitopes in VP-3 of LDV (Harty and Plagemann, 1988) and $G_L$ of EAV (Balasuriya et al., 1995) was demonstrated using monoclonal antibodies and sequencing escape mutants. More recent studies indicate that protein E plays a role in inducing neutralizing antibodies (Persch et al., 1995).

A modified-live-virus vaccine strain RespPRRS® of PRRSV is currently used in the United States for the prevention of the respiratory facet of the syndrome. Although the vaccine strain is attenuated, it, like virulent field strains of PRRSV, has the ability to persist for at least several weeks in a vaccinated pig. Consequently, the source of PRRSV isolated from diagnostic samples is sometimes in question and it would be highly desirable to have a positive assay for identifying the source.

SUMMARY OF THE INVENTION

We have now discovered that ORF 5 can be targeted in a restriction enzyme analysis for distinguishing vaccine strain RespPRRS® of PRRSV from virulent field strains and also for distinguishing field strains from one another. The reading frame is first converted to a double stranded DNA, amplified, and then cut with restriction enzymes in conserved regions which collectively have sufficient variability among strains to permit generation of a unique fragment profile for each strain of PRRSV.

In accordance with this discovery, it is an object of the invention to provide a tool for distinguishing vaccine strain RespPRRS® from wild-type field strains.

It is also an object of the invention to provide a tool for epidemiological studies in the evaluation of the source and transmission of field strains of PRRSV.

It is also an object of the invention to provide a sensitive, reliable, and rapid assay for PRRSV suitable for large-scale herd screening.

A further object of the invention is to provide a diagnostic basis for designing an effective control program for PRRS in swine herds.

Other objects and advantages of this invention will become readily apparent from the ensuing description.

BRIEF DESCRIPTION OF THE DRAWINGS

Figure 2B:
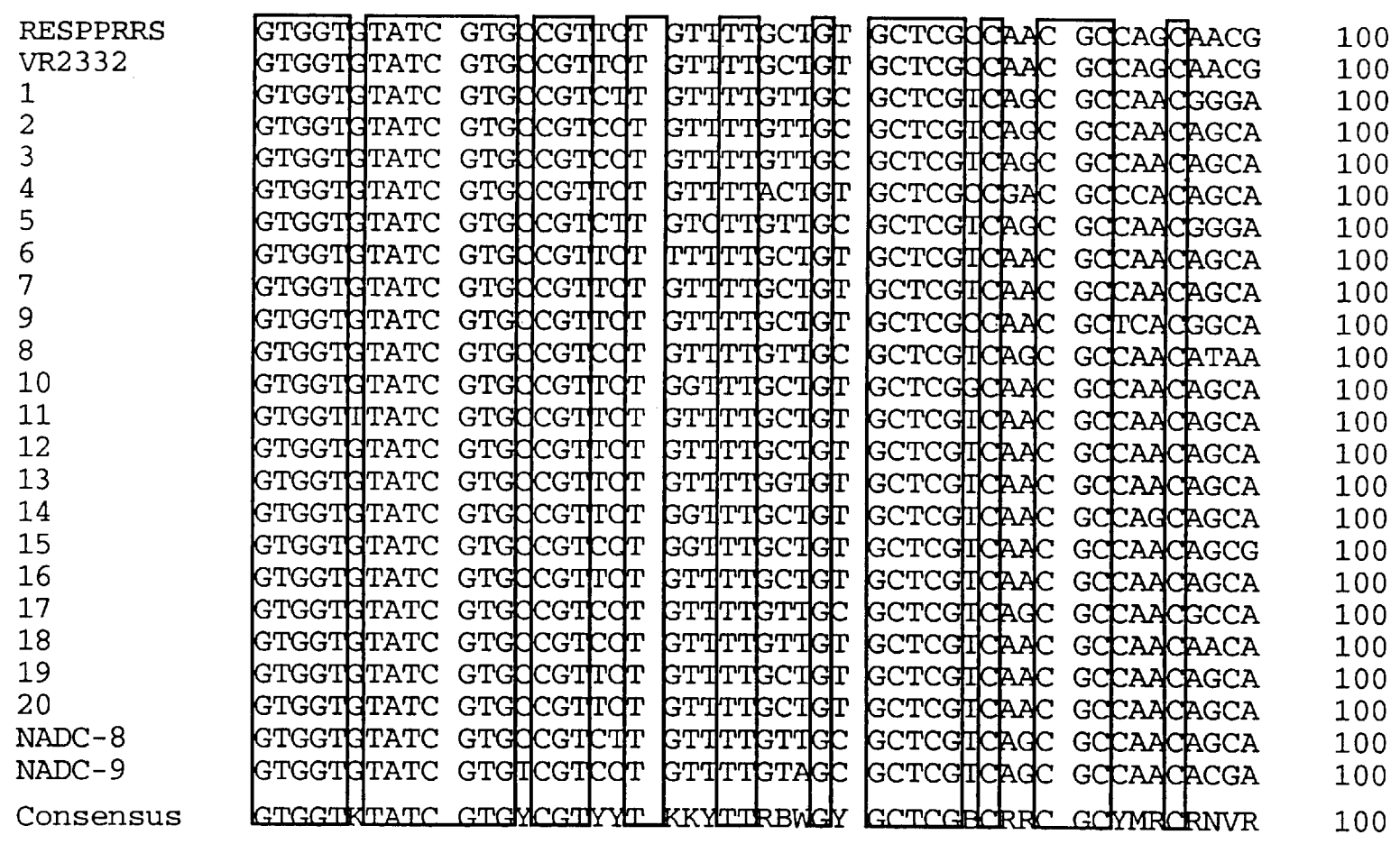
Figure 2D:
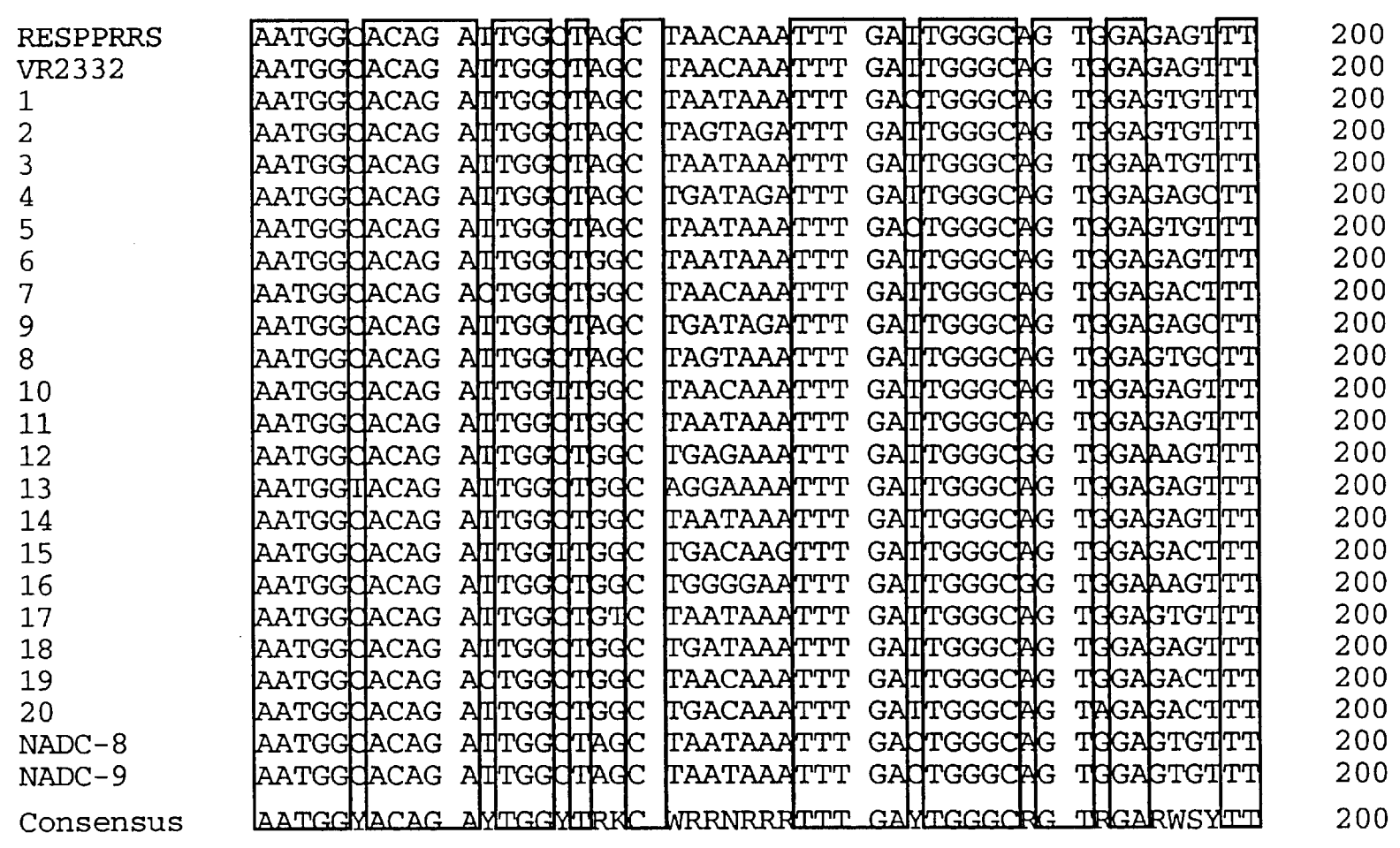
Figure 2E:
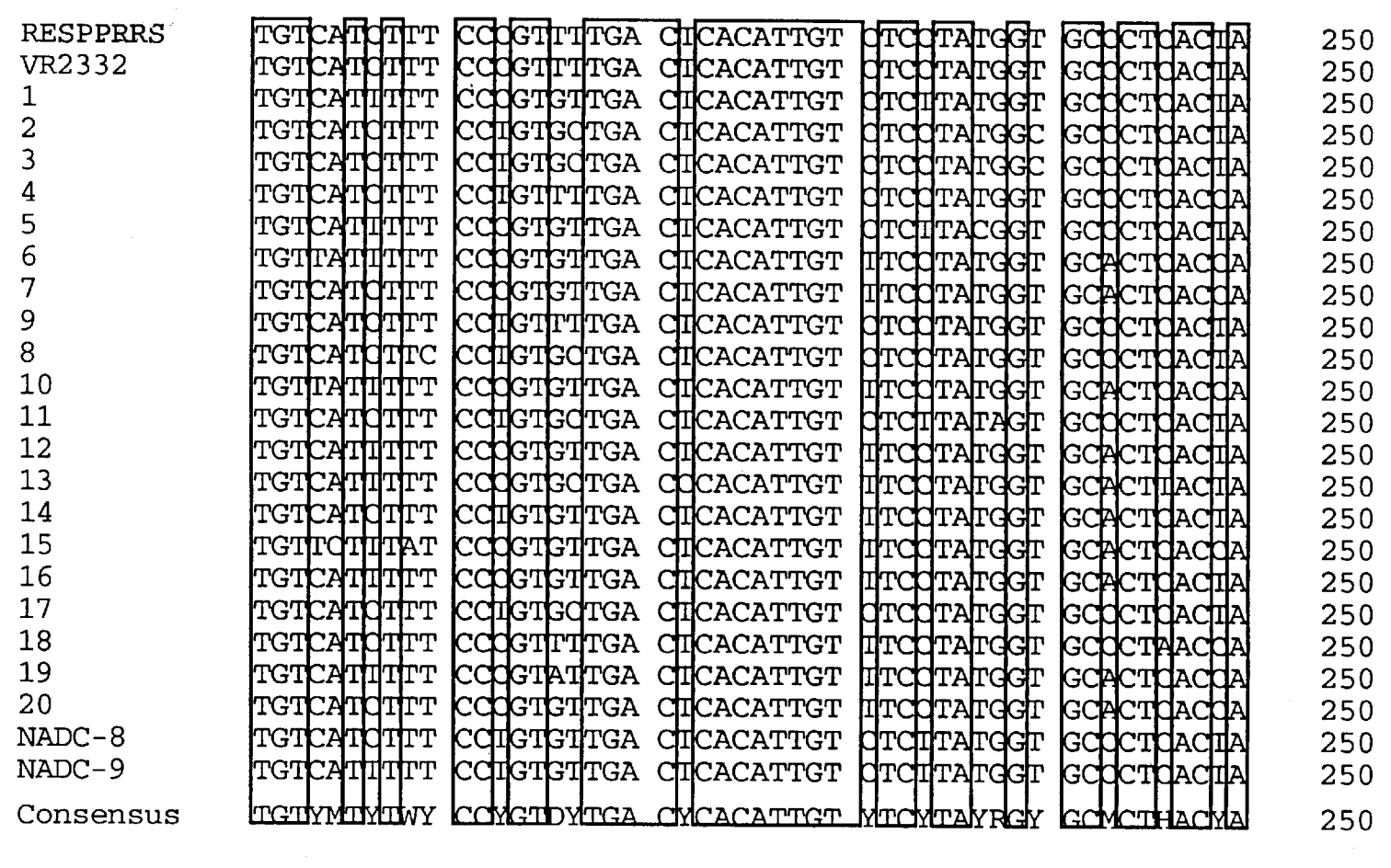
Figure 2F:
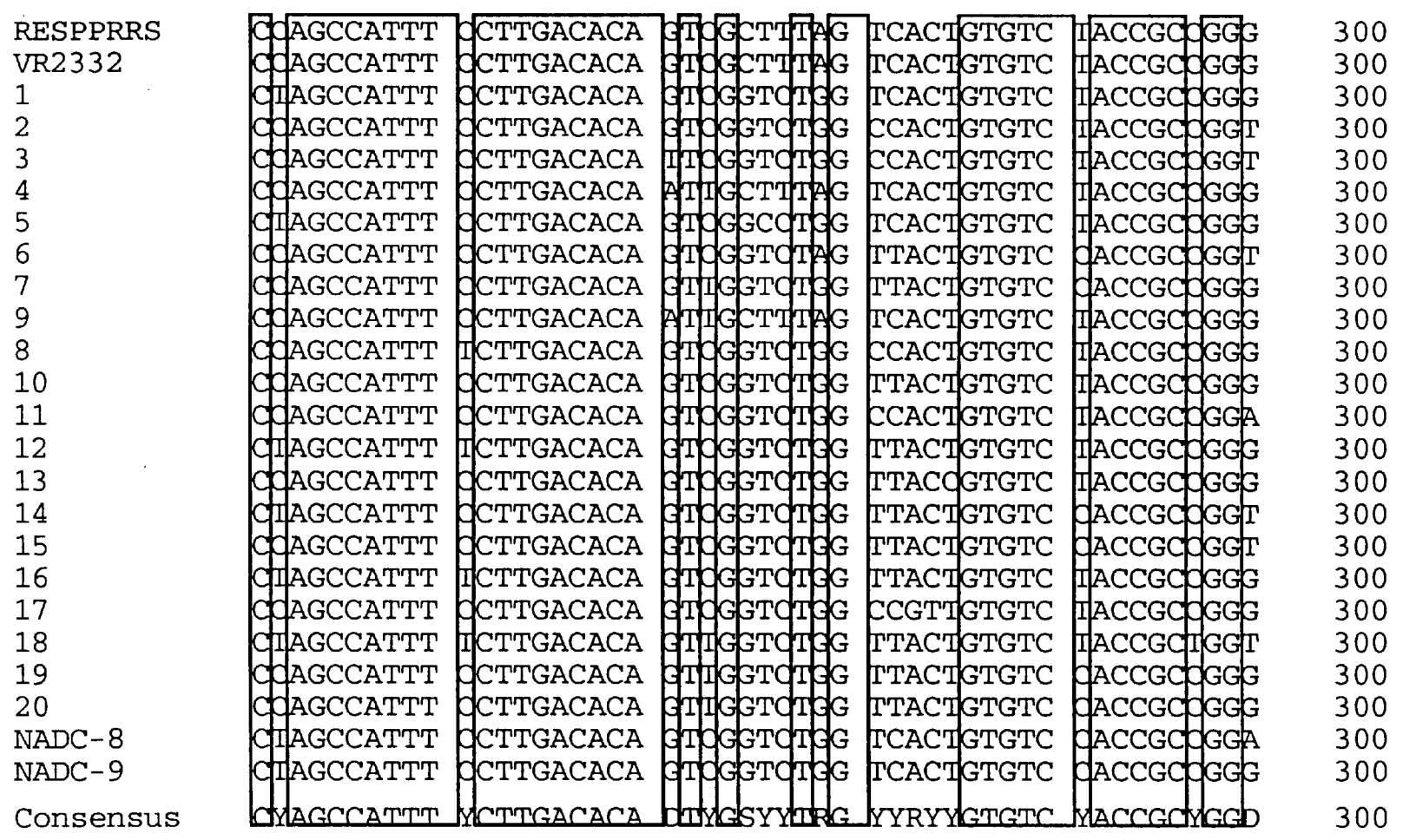
Figure 2G:
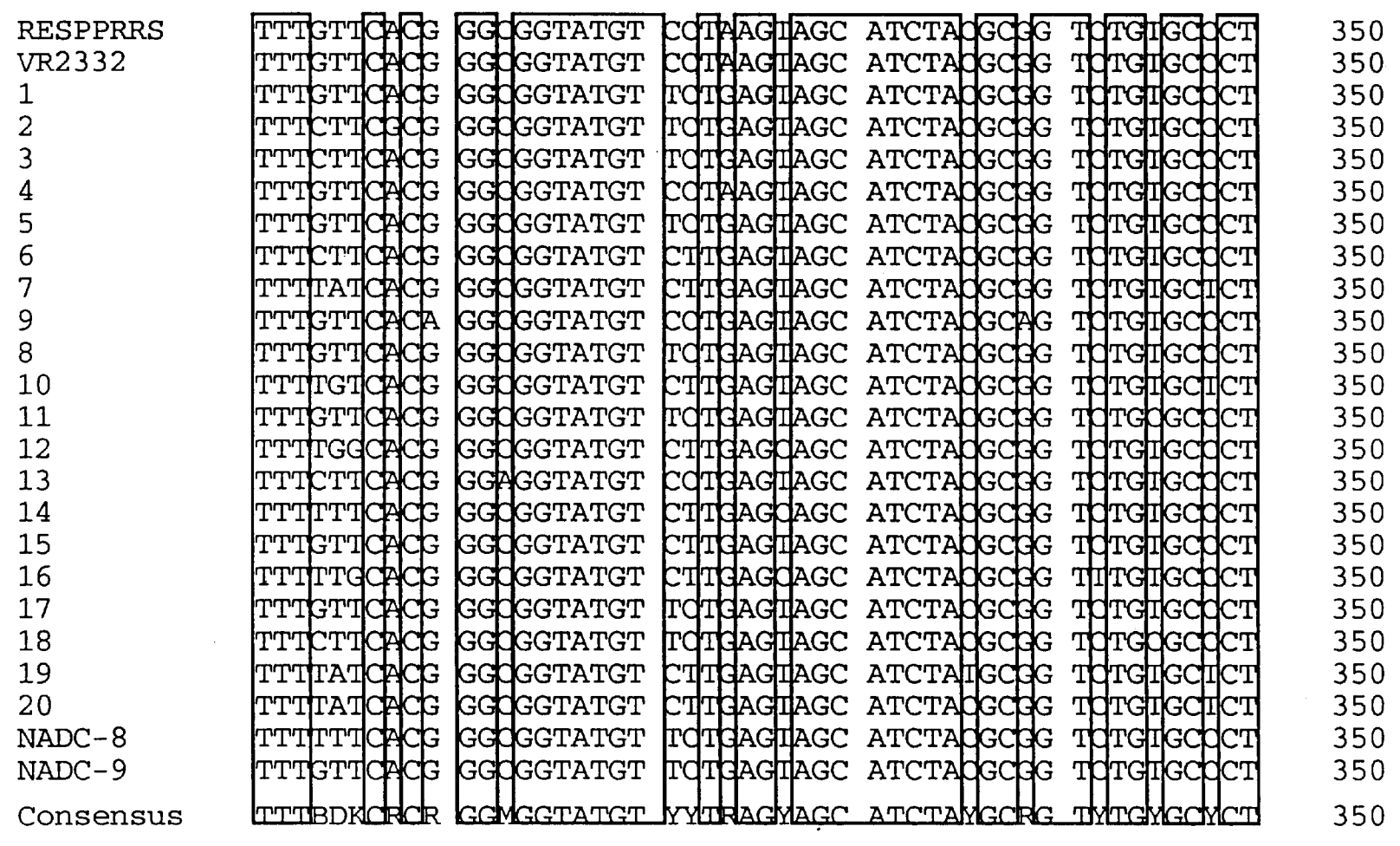
Figure 2H:
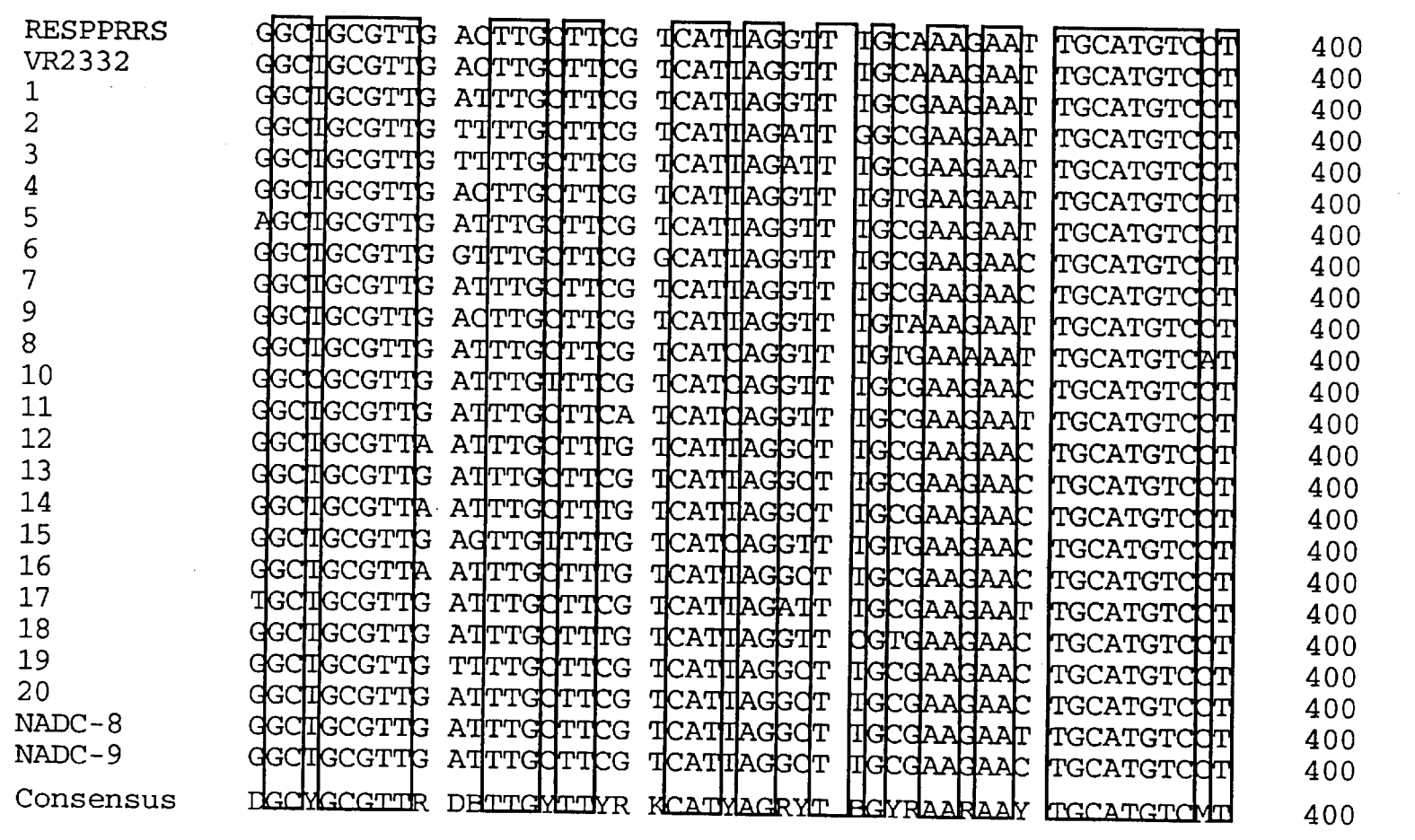
Figure 2J:
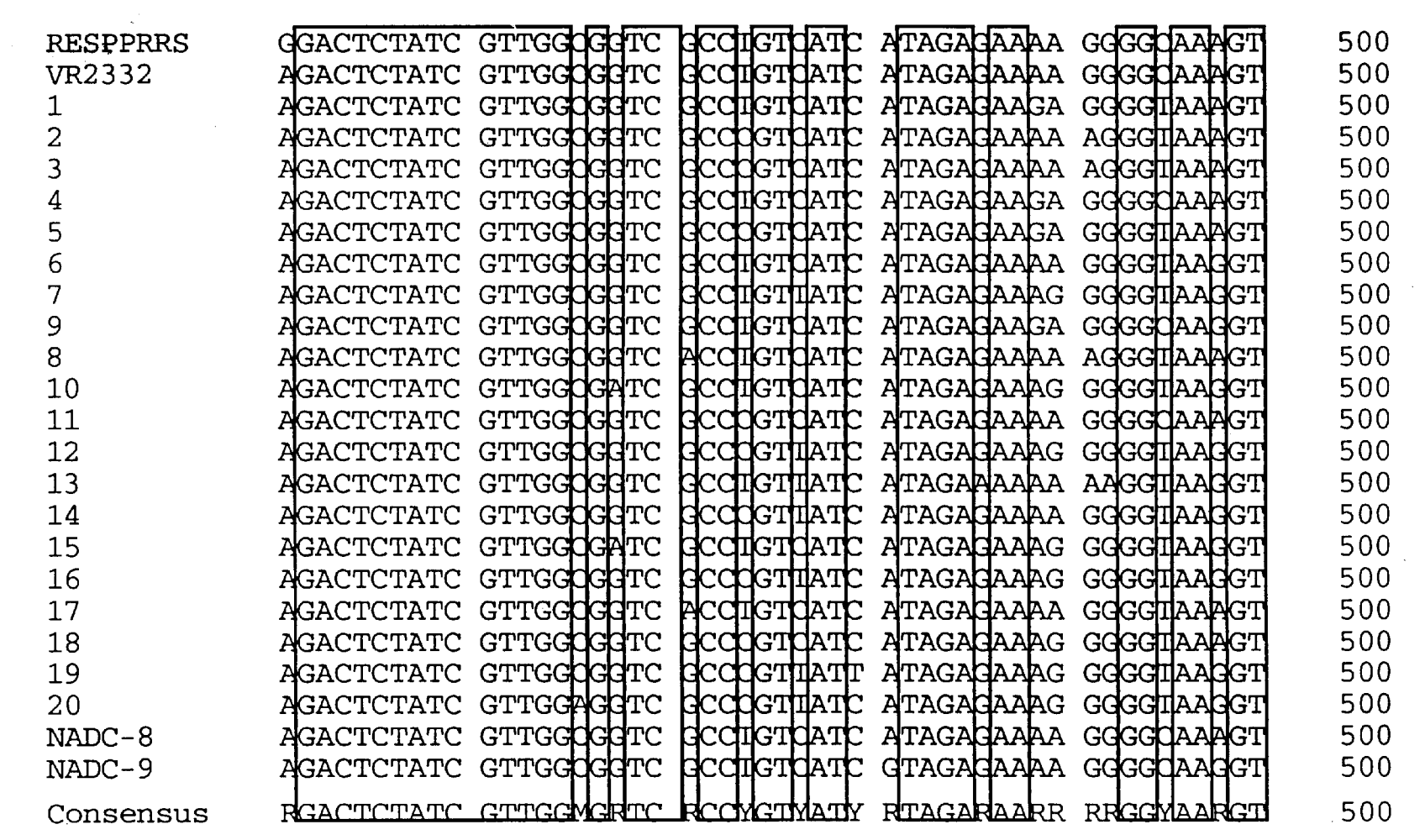
Figure 2K:
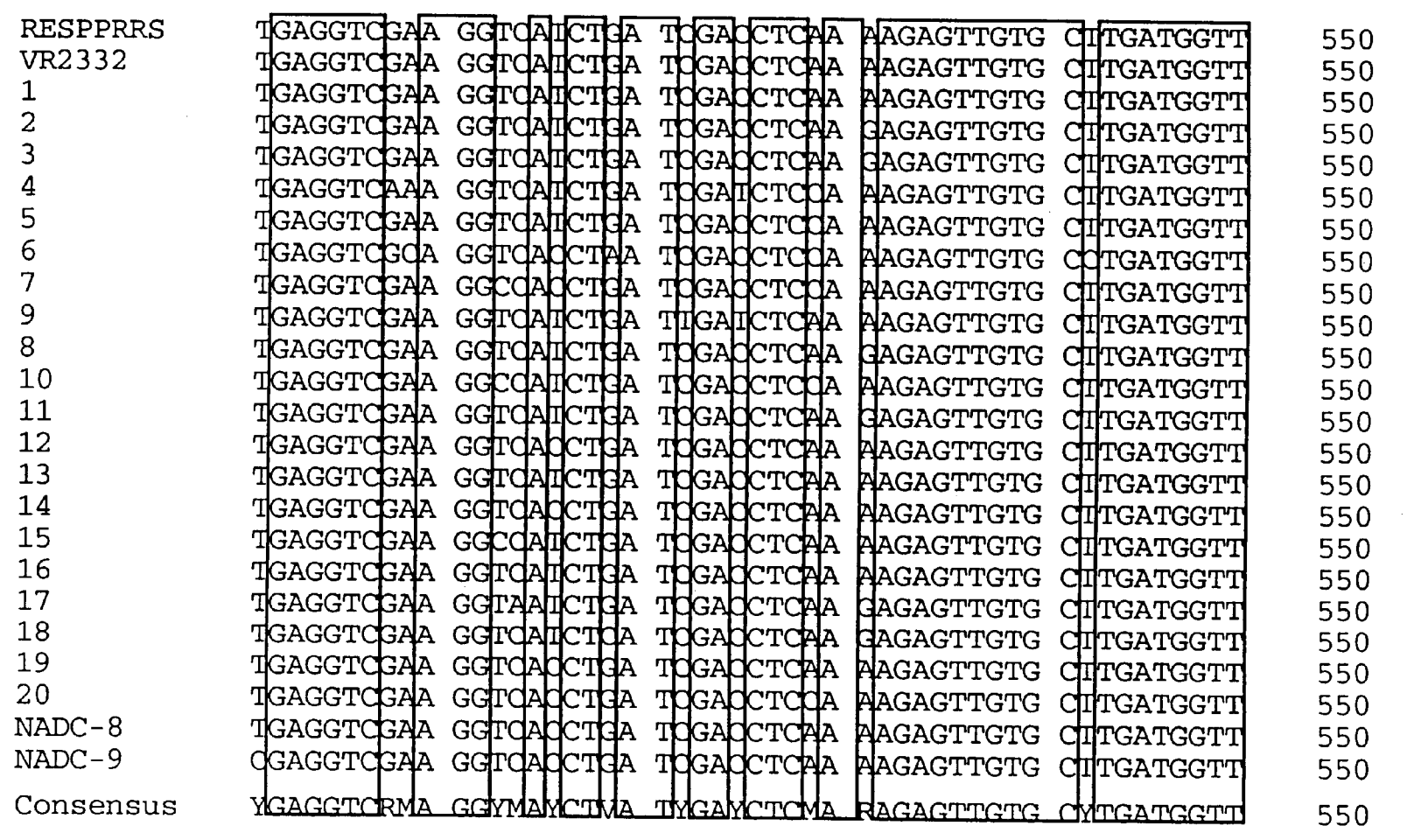
Figure 2L:
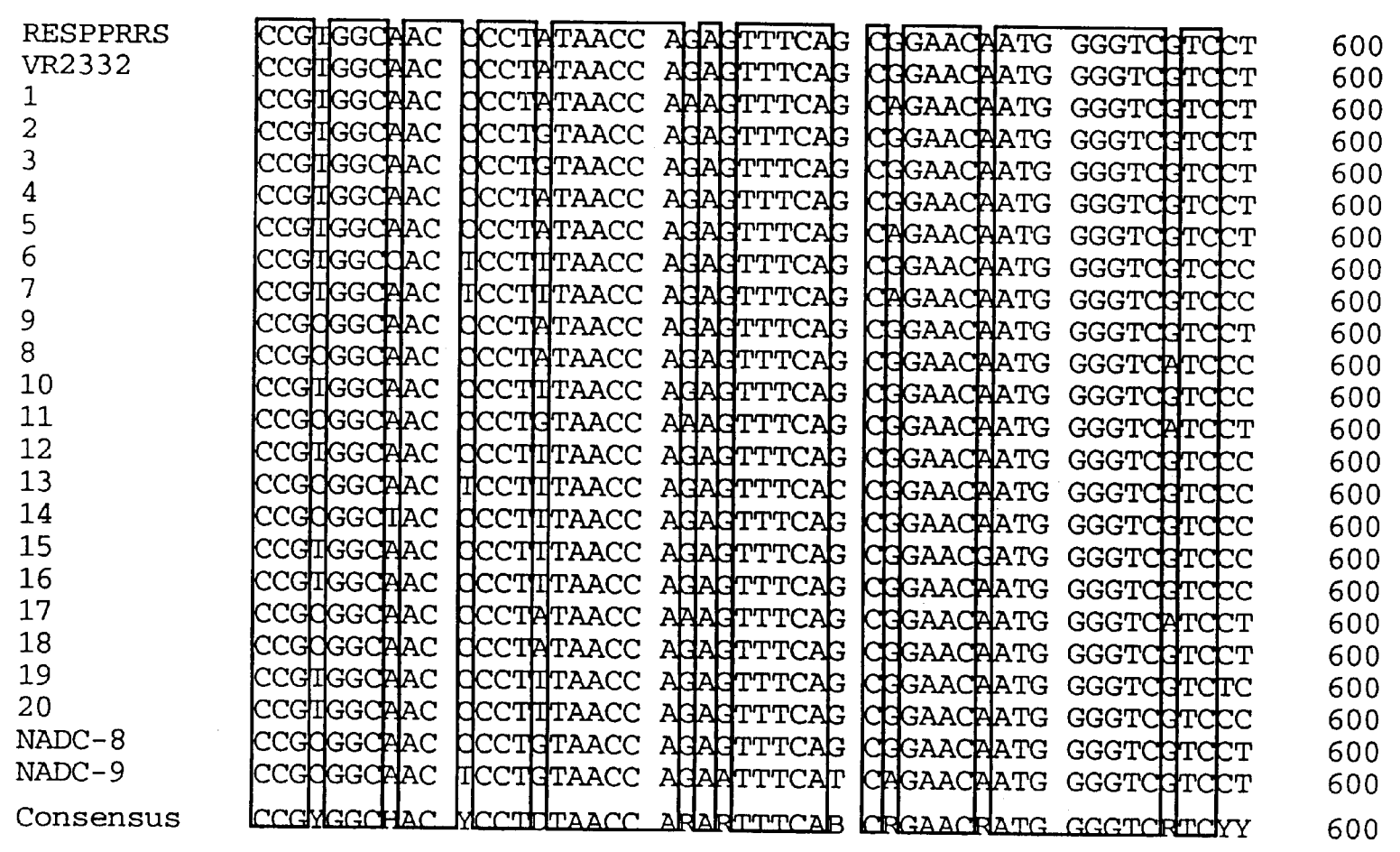

FIG. 2 shows the aligned ORF 5 nucleotide sequences for the 22 field strains and strain RespPRRS® of PRRSV sequenced in conjunction with the invention, and for strain VR 2332 (previously sequenced by others) as compared to the consensus sequence.

DETAILED DESCRIPTION OF THE INVENTION

The primary points of novelty regarding the identification and distinction of individual strains of PRRSV in accordance with this invention include: (1) identification of a segment of the viral genome that is sufficiently variable among strains to allow differentiation, yet stable enough so that there is a low probability of mutational changes during repeated in vitro or in vivo passages of a particular strain; (2) selection of a universal set of primers that allows for reverse transcription (RT) and polymerase chain reaction (PCR) amplification of this segment; and (3) identification of unique restriction sites that allow for the differentiation of vaccine strains from field strains, and field strains from one another.

Figure 1C:
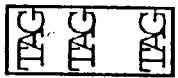
FIG. 1 shows the aligned ORF 5 sequences for field strain VR 2332 and vaccine strain RespPRRS® of PRRSV as well as the consensus sequence for these strains.

Insofar as currently known, ORF 5 is the only region of the PRRSV genome that has the proper combination of nucleotide variability among strains of PRRSV (exemplified by those listed in Table I) together with long term stability to allow for restriction enzyme differentiation. On the other hand, the stability of the ORF 5 nucleotide sequence of a particular strain is indicated (FIG. 1) by the fact that there are only two base differences (positions 38 and 451) between vaccine strain RespPRRS® (indicated in the figure as "resp.PRRS"), which was attenuated by repeated serial passages in cell culture, and its presumed parental strain VR 2332. These two strains (which could be considered variations of the same strain) are indistinguishable on the basis of restriction patterns associated with any of the 77 restriction enzymes reported in Table II.

FIG. 2 clearly depicts variations in the ORF 5 nucleotide sequences for strain RespPRRS® of PRRSV sequenced in conjunction with the invention and for 23 field strains of PRRSV, including 22 field strains sequenced in conjunction with the invention and VR 2332 (the sequence of which was previously reported in the literature). The consensus sequence for the 24 strains is also given in the figure. The position and frequency of these variations are sufficient to permit differentiation of every field strain (except presumed parental strain VR 2332) from the vaccine strain using a singular enzyme, either Mlu I or Sfc I (see Tables I and II). Assaying with both enzymes provides confirmation. As best shown in Table I, a high degree of assurance can be obtained by comparing the combined fragment patterns from Mlu I, Sfc I, Hinc II, and Sac II. All 23 of the field strains in Table I can be differentiated from one another by means of an appropriate combination of six or fewer restriction enzymes selected by reference to Table II. In Table II, the PRRSV strains are shown across the top and 77 enzymes which were evaluated for purposes of the invention are indicated on the left. The last column represents the cut sites for both strain RespPRRS® and its presumed parental strain VR 2332. Even though there are two base differences between the ORF 5 of these two strains, the cutting sites in the respective ORF 5 cDNAs are the same for all of the 77 enzymes shown in the table. The numbers shown in the table cells represent the size of the resultant fragments obtained by cutting a 716 bp amplified DNA including the ORF 5. Multiple fragment sizes are listed in order from 5' to 3'. The symbol "xxx" indicates that the particular enzyme does not cleave anywhere within the 716 bp fragment.

Given that the PRRSV genome is RNA, the region coding for ORF 5 must first be reverse transcribed by methods known in the art to produce double stranded cDNA. By means of PCR or any other like process, the coding region is then amplified to the extent necessary for the subsequent restriction enzyme analysis. Primers are preferably selected from nearby flanking regions upstream and downstream from the reading frame.

EXAMPLE 1

Cell and Virus Propagation

MARC-145 cells (Kim et al., 1993, herein incorporated by reference) were cultured in Eagle's minimum essential medium (MEM), supplemented with 5% fetal bovine serum (FES) and antibiotics. Twenty-two field stains of PRRSV isolated from Canada, Guatemala, and the United States as well as vaccine strain RespPRRS® of PRRSV were propagated and then cloned by three rounds of end point dilutions on MARC-145.

RNA Extraction and Reverse Transcriptase Polymerase Chain Reaction

Viral RNA was isolated from 22 field strains and vaccine strain RespPRRS® of PRRSV (see Table I) using a standard guanidinium isothiocyanate method (Sambrook et al., 1989, herein incorporated by reference). Single tube reverse transcriptase polymerase chain reactions (RT-PCR) as described by Sellner et al. (1992, herein incorporated by reference) with slight modifications were conducted on RNA isolated from each of the 23 strains in a Perkin-Elmer 4800®. Primers were designed based on the nucleotide sequence of field strain VR 2385 (Meng et al., 1995; Morozov et al., 1995, both herein incorporated by reference) and synthesized by Integrated DNA Technologies, Inc. (Coralville, Iowa). The sense primer was 5'-CCATTCTGTTGGCAATTTGA-3' (SEQ ID NO:25) and the anti-sense primer was 5'-GGCATATATCATCACTGGCG-3'(SEQ ID NO:26). In SEQ ID NO:27 (which is similar to SEQ ID NO:23 for ORF 5 of vaccine virus RespPRRS but additionally shows the immediate flanking regions), the sense primer extends from nucleotide 1 through nucleotide 20 and the antisense primer is the complement to the nucleotide sequence extending from nucleotide 716 to 697. A 716 bp piece encompassing ORF 5, with flanking regions of ORF 4 and ORF 6, was generated for all strains and the fragments were purified using a GENECLEAN® kit (Bio 101).

Sequencing

Double stranded nucleotide sequencing (Tabor and Richardson, 1987, herein incorporated by reference) with Taq polymerase and fluorescently labelled dideoxynucleotides (Applied Biosystems International, Prism System) as described in Sanger et al. (1977, herein incorporated by reference) was performed in triplicate on both strands for analysis with an Applied Biosystems 373A® automated sequencer. The same primer set as described above was used for sequencing. Nucleotide sequence editing and alignments were performed using Intelligenetics, GENEWORKS® version 2.2 software.

Analysis

To determine the rate of possible drift of ORF 5 sequence, four PRRSV strains of U.S. origin: NADC-8, NADC-9, 41572-2, and 18310-A were repeatedly passed on MARC-145 cells. NADC-8, NADC-9, and 41572-2 encountered 61 passages, and 18310 encountered 31 passages. RT-PCR was performed and the subsequent product was sequenced as described above.

Sequencing of the four selected strains passed in vitro revealed: 6 nucleotide and 4 amino acid substitutions (2,110, 136,194 a.a.) for NADC-8; 2 nucleotide and 1 amino acid substitution (59 a.a.) for NADC-9; 2 nucleotide and 2 amino acid substitutions (3, 34 a.a.) for strain 41572-2; and 4 nucleotide and 2 amino acid substitutions (3,194 a.a.) for strain 18310-A (data not shown). However, none of these changes affected restriction patterns of any of these four strains.

Comparison of Sequences

The complete ORF 5 gene sequence for each of 22 PRRSV field strains and for the vaccine strain RespPRRS® was determined. The sequences for the field strains are shown in the SEQUENCE LISTING as SEQ ID NOs:1–22, that for field strain VR 2332 (previously published) is shown as SEQ ID NO:24, and that for vaccine strain RespPRRS® is shown as SEQ ID NO:23. These sequences were aligned and compared (FIG. 2) to the consensus sequence for all 24 strains. Alignment analysis indicates the same initiation and termination sites exist for all 24 strains. Regions of high and low variability are also apparent. Insertions and deletions were found to be nonexistent on the nucleotide level.

EXAMPLE 2

To differentiate the vaccine strain RespPRRS® and the presumed parental field strain VR 2332 from the 22 remaining (field) strains shown in Table I, it was necessary to select one or more appropriate restriction enzymes. The selection was based on a comparison of the ORF 5 sequence data for these strains in conjunction with the known cut sites for the enzymes as summarized in Table II. Using this technique, enzymes Mlu I, Sfc I, Hinc II and Sac II were initially selected. The enzymes Mlu I and Sfc I cut only the vaccine strain RespPRRS® and field strain VR 2332, and do not cut any of the other 22 PRRSV strains shown in Tables I and II.

The restriction enzymes Hinc II and Sac II cut most of the PRRSV strains tested giving various gel patterns. Only strains 4 and 9 have a Hinc II gel pattern identical to the RespPRRS®/VR 2332 gel pattern. A second gel analysis with Sac II differentiates the vaccine strain and VR 2332 from PRRSV field strains 4 and 9. The combined results with the 4 restriction enzymes give a high degree of assurance of the RespPRRS®/VR 2332 genotype.

Restriction enzymes Mlu I and Sfc I are particularly valuable for differentiation because these enzymes cut only strain RespPRRS®/VR 2332 and none of the other 22 strains of PRRSV. Mlu I recognizes the 6 base pair sequence A'CGCGT. For the other 22 PRRSV strains, there are two base differences, namely, guanines at positions 409 and 411; both need to occur in order to create a functional Mlu I site. Since two bases need to change for the other strains of PRRSV, the Mlu I pattern is a strong marker for the RespPRRS®/VR 2332 genotype. Also Sfc I only cuts the RespPRRS®/VR 2332 PCR-amplified DNA fragment. However, 9 of the 22 other strains of PRRSV require only a single nucleotide change, in the localized 6-nucleotide cutting site, to create a functional Sfc I site. Therefore, mutations resulting in Sfc I cutting are potentially more frequent than those for Mlu I cutting. As a safeguard against erroneous identification resulting from such mutations, it is advisable to conduct the assay with additional enzymes.

Figure 3:
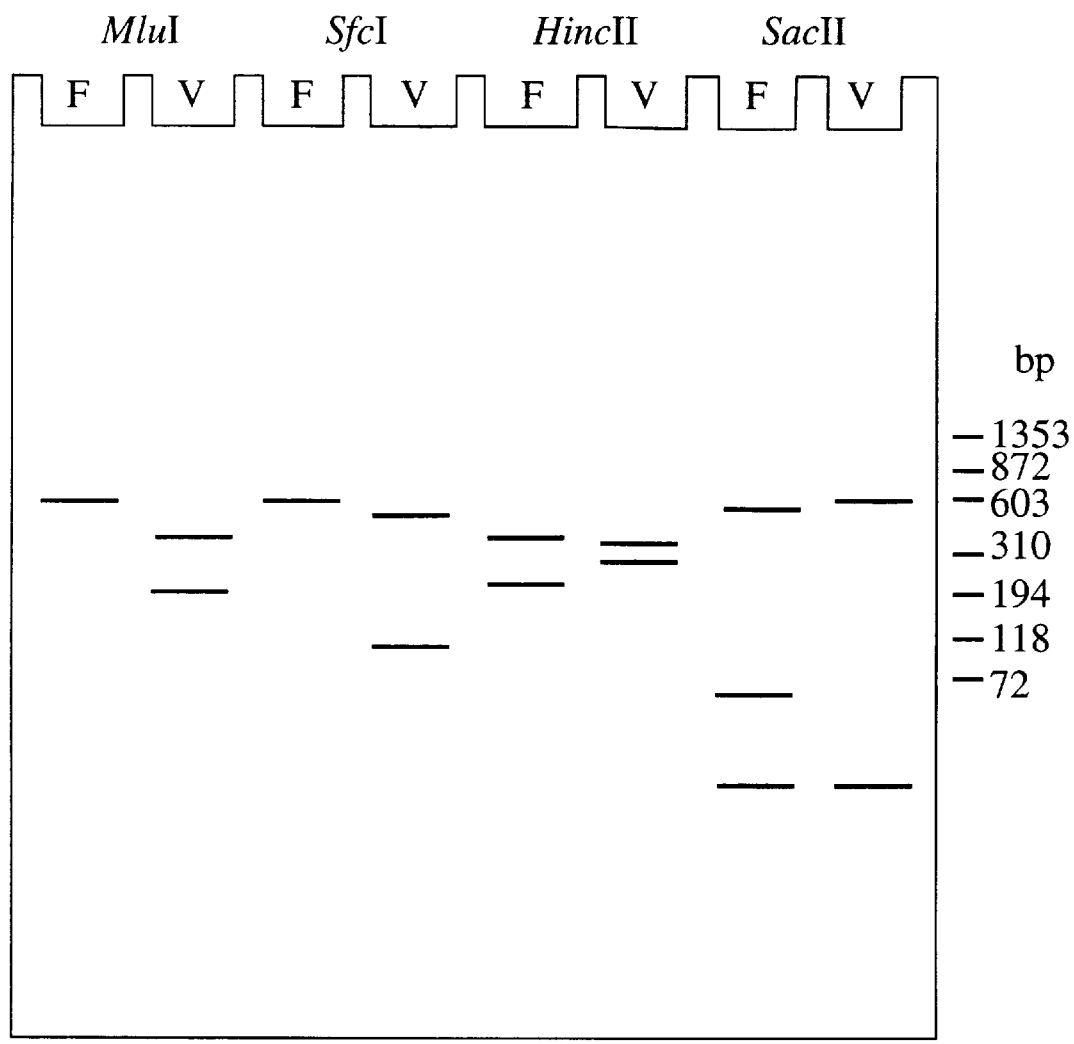
FIG. 3 is a computer generated schematic diagram of Mlu I, Sfc I, Hinc II and Sac II ORF 5 cDNA fragments for PRRSV field strain NADC-8 (F) and vaccine strain RespPRRS® (V).

A typical gel electrophoresis test, in which vaccine strain RespPRRS® and strain NADC 8 are compared after digestion with Mlu I, Sfc I, Hinc II and Sac II, is represented by FIG. 3. The Mlu I and Sfc I gel patterns of strain NADC 8 are the same for all 22 PRRSV strains and distinct from strain RespPRRS®/VR 2332 gel pattern. For restriction enzymes Hinc II and Sac II, strain NADC-8 gel patterns are also distinct from strain RespPRRS®/VR 2332 patterns, but similar to other PRRSV strains. However, all of the PRRSV strains in Table II can be differentiated one from another by appropriate selection of restriction enzymes. No more than 6 restriction enzymes would be needed for differentiating the strains reported in Table II.

EXAMPLE 3

The constancy of the restriction enzyme pattern within ORF 5 during persistent infection of pigs with PRRSV was evaluated for the purpose of assessing the validity of the assay described in Example 2. Virus stability upon PRRSV replication in vivo was studied in four individual gilts, in penmates, and in gilt-piglet relationships. The results are shown in Table III, below. In each of evaluations Nos. 1–3, the virus was passaged in vivo in a gilt for a period of 7 weeks. After this time, virus was isolated from a sample taken by lung lavage wherein the alveolar macrophages, which are believed to be the primary cells for virus replication in vivo, are flushed from the lung. In each case, the recovered strain was characterized by the same RE pattern as the exposure strain (RespPRRS®). In evaluation No. 4, the same results were obtained for strain NADC-8. In evaluation Nos. 5 and 6, a pig was exposed to strain NADC-8, and 8 weeks later brought into contact with a second pig which thereafter shared the same pen. After 3 weeks, the RE pattern of the strain recovered from the second pig was identical to that of Strain NADC-8 used to infect the first pig. In evaluation No. 7, a pregnant gilt was infected with strain RespPRRS® eight weeks prior to farrowing. The RE pattern of the PRRSV recovered 5 weeks later from one of her piglets was the same as the original strain RespPRRS®.

It is understood that the foregoing detailed description is given merely by way of illustration and that modifications and variations may be made therein without departing from the spirit and scope of the invention.

TABLE I

Restriction Enzyme Analysis of PRRSV Isolates

| Strains | ID | Origin | Year | Restricted Enzyme[a] | | | |
|---|---|---|---|---|---|---|---|
| | | | | MluI | SfcI | HincII | SacII |
| 1 | 46448 | IA | 1989 | — | — | 219 | 24 |
| 2 | 46907 | KY | 1991 | — | — | — | 24 |
| 3 | 1205-D | MO | 1992 | — | — | — | 24 |
| 4 | 10654 | IA | 1992 | — | — | 360 | — |
| 5 | 30093-A | IL | 1992 | — | — | 219 | 24 |
| 6 | 34075 | NE | 1992 | — | — | 88,219 | 24 |
| 7 | 49138 | TX | 1992 | — | — | 88,219 | 24 |
| 8 | 5556 | MI | 1993 | — | — | — | 24,555 |
| 9 | 22805 | KS | 1992 | — | — | 360 | 555 |
| 10 | 5591 | NC | 1993 | — | — | 219 | 24 |
| 11 | 14622 | AR | 1993 | — | — | 88 | 24,555 |
| 12 | 19950-E | MN | 1993 | — | — | 88,219 | 24 |
| 13 | 26948-2 | VA | 1993 | — | — | 88 | 24,555 |
| 14 | 41572-2 | NE | 1993 | — | — | 88,219 | 24,555 |
| 15 | 42928 | IL | 1993 | — | — | 88,219 | 24 |
| 16 | 32983-LG | NC | 1993 | — | — | 88,219 | 24 |
| 17 | 30352-3 | MI | 1993 | — | — | — | 24,555 |
| 18 | 47324-2 | Canada | 1993 | — | — | 88 | 24,555 |
| 19 | 18310-A | PA | 1994 | — | — | 88 | 24 |
| 20 | 24901 | Guatemala | 1994 | — | — | 88,219 | 24 |
| NADC-8 | (IA)-92 | IA | 1992 | — | — | 219 | 24,555 |
| NADC-9 | (IA)-93 | IA | 1993 | — | — | 219 | 24,555 |
| RespPRRS ® | — | MN[b] | | 408 | 116 | 360 | 24 |
| VR 2332 | — | MN | | 408 | 116 | 360 | 24 |

[a]The designated cut sites are for the 603 bp ORF 5
[b]Presumed to originate from strain VR 2332.

TABLE II

| ENZYME | #1 | #2 | #3 | #4 | #5 | #6 | #7 | #8 | #9 | #10 | #11 | #12 |
|---|---|---|---|---|---|---|---|---|---|---|---|---|
| Acc I | 318 | 318 | 318 | 318 | 318 | xxx | xxx | 318 | 318 | 318 | 318 | 318 |
| Aha II | xxx | 268 | 268 | 118 | xxx | xxx | xxx | xxx | xxx | xxx | xxx | xxx |
| Alu I | multi(4) | multi(4) | multi(4) | multi(4) | multi(5) | 136/176 | 136/176 | 136/176/198 | multi(4) | 136/176 | 136/176 | 136/176 |
| Apa LI | xxx | xxx | 204 | xxx | xxx | 268 | 268 | xxx | xxx | 268 | 268 | 268 |
| Apo I | 140/204 | 309 | 309 | xxx | 140/204 | 204 | 204 | 204 | xxx | 204 | 204 | 204 |
| Bal I | xxx | xxx | xxx | xxx | xxx | 585 | xxx | 309 | xxx | xxx | 309 | xxx |
| Bsn I | 267 | 267 | 267 | 267 | 267 | xxx | xxx | 267 | 267 | xxx | xxx | xxx |
| Bbv | 145/368 | 145/368 | 145/368 | 145/368 | 145/368 | 145/368 | 145/368 | 142/145/368 | 145/368 | 145 | 145/368 | multi(5) |
| Bfa I | 195/280 | 195/199 | 195 | 195/445 | 195/280/378 | 306/465/629 | 465/629 | 195/199/629 | 195/445 | 629 | xxx | 280/465/629 |
| Bse HII | xxx | xxx | 268 | 118 | xxx | xxx | xxx | xxx | xxx | xxx | xxx | xxx |
| Bsa JI | 49/376/580 | 49/376/580 | 49/376/580 | 49/376/580 | 49/580 | multi(4) | 49/580 | 49/376/560 | 49/376/580 | 49/580 | 49/376/580 | 49/376/580 |
| Bsi EI | 498 | 498 | xxx | 498 | 498 | 498 | 498 | xxx | 498 | 498 | 498 | 498 |
| Bal I | xxx | xxx | xxx | xxx | xxx | xxx | 325 | xxx | xxx | xxx | xxx | 331 |
| Bsm AI | 263 | 263 | 263 | 263 | 263 | xxx | 216 | 263 | 263 | 263 | 263 | xxx |
| Bsp 1286I | 272/377 | 377 | 377 | 112/272/377 | 272/377 | 112/272/377 | 112/272/377 | 272/377 | 112/272/377 | 112/272/377 | 112/272 | 112/272/377 |
| Bsr FI | 216 | 324 | 324 | xxx | xxx | 324 | xxx | xxx | xxx | xxx | xxx | xxx |
| Bsr I | xxx | xxx | xxx | xxx | 216 | xxx | 195 | xxx | xxx | xxx | xxx | xxx |
| Bst EII | 510 | xxx | xxx | xxx | xxx | 540 | xxx | 496 | xxx | xxx | xxx | 540 |
| Bst WI | 378/428 | 378/428 | 378/428 | 378/428 | 306/428 | 378/428 | 428 | 378 | 378/428 | 428 | 378/428 | 378/428 |
| Bst UI | 51/366 | xxx | 51/65/366 | 65/366 | 51/366 | 51/366 | 51/65/366 | multi(4) | 65/582 | multi(4) | multi(4) | 51/65/366 |
| Cfr 10I | xxx | 324 | 324 | xxx | xxx | 324 | xxx | xxx | xxx | xxx | xxx | xxx |
| Cla I | xxx | xxx | xxx | 550 | xxx | xxx | xxx | xxx | xxx | xxx | xxx | xxx |
| Dde I | 351/472/628 | 351/472/628 | 351/472/628 | 351/172/628 | 351/472/628 | xxx | 472 | 351/472 | 351/472/628 | 472 | 351/472/628 | 199/472 |
| Dpn I | 549 | 549 | 549 | 549/553 | 549 | xxx | 549 | 549 | 553 | 497/549 | 549 | 549 |
| Dpn II | 547 | xxx | 547 | 547/551 | 547 | xxx | 547 | 547 | 551 | 495/547 | 547 | 547 |
| Eas I | xxx | 307 | 307 | xxx | xxx | 583 | xxx | 307 | xxx | 379 | 307 | xxx |
| Ear I | 510 | xxx | xxx | 510 | 510 | xxx | xxx | xxx | 510 | xxx | xxx | xxx |
| Eco 47III | xxx | xxx | xxx | xxx | xxx | xxx | xxx | xxx | xxx | xxx | xxx | xxx |
| Esp 3I | xxx | xxx | xxx | xxx | xxx | xxx | xxx | xxx | xxx | xxx | xxx | xxx |
| Fnu 4HI | 134/382 | 134/382 | 134/382 | 134/382 | 134/382 | 134/382 | 134/382 | multi(4) | 134/382/583 | 134/382 | 134/382/583 | multi(5) |
| Fok I | xxx | xxx | xxx | xxx | xxx | xxx | xxx | 610 | xxx | xxx | 610 | xxx |
| Hae II | 121/434 | 121/271/434 | 121/271/434 | 434 | 121/434 | 434 | 434 | 121/434 | 434 | 434 | 434 | 434 |
| Hae III | 309 | 309 | 309 | xxx | 304 | 585 | 541 | 309 | xxx | 381/541 | 309 | 547 |
| Hga I | xxx | xxx | xxx | 126/173 | 173 | 173 | 173 | 173 | 173 | 173 | 173 | 173 |
| Hgi AI | xxx | xxx | xxx | 112 | xxx | 112/272 | 112/272/377 | xxx | 112 | 112/272/377 | 112 | 112/272 |
| Hhe I | 110/120/433 | xxx | 433 | 433 | 110/120/433 | 433 | 433 | 110/120/433 | 433 | 433 | 375/433 | 433 |
| Hinc II | 247 | 247 | 248/481 | 388 | 247 | 116/247 | 116/247 | xxx | 388 | 247 | 116 | 116/247 |
| Hinf I | 248/481 | 248/481 | 248/481 | 248/481 | 248/481 | 248/481 | 248/481 | 248/481 | 248/481 | 248/481 | 248/481 | 248/481 |

| ENZYME | #13 | #14 | #15 | #16 | #17 | #18 | #19 | #20 | REF:V2332 |
|---|---|---|---|---|---|---|---|---|---|
| Acc I | | | | | | 318 | xxx | xxx | 318 |
| Aha II | | | | | | xxx | xxx | xxx | xxx |
| Alu I | 136/176 | 136/176 | 138/176 | 136/176 | 136/175 | 136/176 | 136/176 | 136/176 | multi(4) |
| Apa LI | 268 | 268 | 268 | 268 | xxx | xxx | 268 | 268 | xxx |

NADC-8  NADC-9
multi(4)  multi(4)
xxx  xxx

TABLE II-continued

| ENZYME | #1 | #2 | #3 | #4 | #5 | #6 | #7 | #8 | #9 | #10 | #11 | #12 |
|---|---|---|---|---|---|---|---|---|---|---|---|---|
| Apo I | 204 | 204 | 204 | xxx | 204 | 204 | 204 | 204 | 204 | 140/204 | 140/204/601 | 204 |
| Bal I | xxx | xxx | xxx | xxx | xxx | xxx | xxx | xxx | xxx | xxx | xxx | xxx |
| Bsn I | xxx | xxx | xxx | xxx | xxx | xxx | xxx | xxx | xxx | 257 | 267 | 267 |
| Bbv I | multi(4) | multi(4) | 145/368 | 431 | 108/118/431 | 431 | 431 | 145/368 | muLi(4) | 145/368 | 145/368 | 145/368 |
| Bfa I | 465/629 | 280/629 | 629 | 266 | 325 | 325 | 325 | 629 | 629 | 325 | 195/280 | 195 |
| Bse HI | xxx | xxx | xxx | xxx | xxx | 266/534 | 266 | 47/490 | xxx | 266 | xxx | 534 |
| Bsa JI | 49/376/580 | multi(4) | 49/376/580 | xxx | xxx | xxx | xxx | xxx | xxx | xxx | xxx | xxx |
| Bsi EI | 498 | 498 | 498 | 195/445 | 195/280/378 | 306/465/629 | 465/629 | 195/199/629 | 49/580 | 629 | 49/376/580 | 49/376/580 |
| Bal I | xxx | xxx | xxx | 308 | 308 | 308/540 | 308 | 496 | xxx | 308/333 | 498 | 498 |
| Bsm AI | xxx | xxx | xxx | 547/551 | 547 | xxx | 547 | 547 | 325 | 495/547 | 593 | xxx |
| Bsp 1286I | 112/272/377 | 112/272/377 | 112/272/371 | 425/453/527 | 425/453/527 | 324/425/453 | 425 | 227/453 | 216/630 | 425 | 425/453 | 263 |
| Bsr FI | xxx | 324 | 324 | xxx | xxx | xxx | xxx | xxx | 112/272/377 | xxx | xxx | 112/272/377 |
| Bsr I | xxx | 540 | xxx | xxx | xxx | xxx | xxx | 195 | xxx | 216 | 216 | xxx |
| Bst EII | 308 | xxx | xxx | 266 | xxx | xxx | xxx | 540 | 540 | 540 | 540 | xxx |
| Bst WI | 378/428 | 378/428 | 98/378/428 | xxx | 325 | 266/465/629 | 266 | 428 | 428 | 378/428 | 378/428 | 378/428 |
| Bst UI | multi(4) | multi(4) | 51/65/366 | 195/445 | 195/280/378 | 306/465/629 | 465/629 | 51/65 | 51/65/366 | 51/366/582 | 51/366/582 | multi(4) |
| Cfr 10I | xxx | 324 | 324 | 308 | 308 | 308/540 | 308 | xxx | xxx | xxx | xxx | xxx |
| Cla I | xxx | xxx | xxx | 547/551 | 547 | xxx | 547 | xxx | xxx | xxx | xxx | xxx |
| Dde I | 351/472 | xxx | 472 | 472 | 351/472/628 | xxx | 351/628 | 472 | 472 | 351/472/628 | 351/472/628 | 351/472/628 |
| Dpn I | 549 | 549 | 497/549 | 47Z | 549 | xxx | xxx | 549 | 549 | 549 | 549 | 549 |
| Dpn II | 547 | 547 | 495/547 | 549 | 547 | xxx | xxx | 547 | 547 | 547 | 547 | 547 |
| Eas I | xxx | xxx | xxx | 547 | 307 | xxx | xxx | xxx | xxx | xxx | xxx | xxx |
| Ear I | xxx | xxx | xxx | xxx | xxx | xxx | xxx | xxx | xxx | xxx | xxx | xxx |
| Eco 47III | xxx | xxx | xxx | xxx | xxx | xxx | xxx | xxx | xxx | xxx | 109 | xxx |
| Esp 3I | xxx | xxx | xxx | xxx | xxx | xxx | xxx | 630 | xxx | xxx | xxx | xxx |
| Fnu 4HI | multi(5) | multi(5) | 134/382 | multi(7) | 134/382/583 | 134/382/583 | 134/382/583 | 134/382 | multi(4) | 134/362/583 | 134/382/583 | 134/382 |
| Fok I | xxx | xxx | xxx | xxx | 610 | xxx | xxx | xxx | xxx | xxx | xxx | xxx |
| Hae II | 434 | 434 | 130/434 | 434 | 121/434 | xxx | 434 | 434 | 434 | 121/434 | 121/434 | 434 |
| Hae III | xxx | xxx | 541 | xxx | 309 | xxx | xxx | xxx | 55 | xxx | xxx | xxx |
| Hga I | 173 | 173 | 173 | 173 | 173 | xxx | 173 | 173 | 173 | 173 | 173 | 173 |
| Hgi AI | 112/272 | 112/272 | 112/272 | 112/272 | xxx | xxx | 112 | 112/272/377 | 112/272/377 | xxx | xxx | 112 |
| Hhe I | 433 | 433 | 129/433 | 433 | 110/120/433 | 324/425/453 | 375/433 | 433 | 433 | 110/120/433 | 110/120/433 | 433 |
| Hinc II | 116 | 116 | 116/247 | 547/551 | 116/247 | xxx | 116 | 116 | 116/247 | 247 | 247 | 388 |
| Hinf I | 481 | 248/481 | 248/461 | 248/481 | 248/481 | 523/564 | 248/481 | 248/481 | 248/481 | 248/481 | 248/481 | 248/481 |

| ENZYME | #1 | #2 | #3 | #4 | #5 | #6 | #7 | #8 | #9 | #10 | #11 | #12 |
|---|---|---|---|---|---|---|---|---|---|---|---|---|
| Hind PI | 108/118/431 | multi(4) | multi(4) | 431 | 108/118/431 | 431 | 431 | 108/118/431 | 431 | 431 | 373/431 | 431 |
| Hpa II | 325 | 325 | 325 | 325 | 325 | 325 | 325 | 325 | xxx | 325 | 325 | 325 |
| Hph I | xxx | xxx | xxx | 266 | xxx | 266/534 | 266 | 47/490 | xxx | 266 | xxx | 534 |
| Kas I | 195/280 | 195/199 | 195 | xxx | xxx | xxx | xxx | xxx | xxx | xxx | xxx | xxx |
| Mae I | 308 | 593 | 593 | 195/445 | 195/280/378 | 306/465/629 | 465/629 | 195/199/629 | 195/445 | 629 | 593 | 280/465/629 |
| Mae III | 308 | 593 | 593 | 308 | 308 | 308/540 | 308 | 496 | 308 | 308/333 | 593 | 308/540 |
| Mbo I | 547 | 547 | 547 | 547/551 | 547 | xxx | 547 | 547 | 551 | 495/547 | 547 | 547 |
| Mbo II | 425/453/527 | 324/425/453 | 324/425/453 | 425/453/527 | 425/453/527 | 324/425/453 | 425 | 227/453 | 453/527 | 425 | 425/453 | 425 |
| Mlu I | xxx | xxx | xxx | xxx | xxx | xxx | xxx | xxx | xxx | xxx | xxx | xxx |
| Mnl I | multi(4) | 282/523/564 | 282/523/564 | 282/453/527 | multi(4) | 523/564 | 471/523/564 | 282/523/564 | 282/510/523 | 523/564 | 282/523/564 | 523/564 |

TABLE II-continued

| ENZYME | #13 | #14 | #15 | #16 | #17 | #18 | #19 | #20 | REF:V2332 |
|---|---|---|---|---|---|---|---|---|---|
| Msc I | xxx | 309 | 309 | xxx | xxx | 309 | 309 | xxx | xxx |
| Mse I | xxx | xxx | xxx | xxx | xxx | xxx | xxx | xxx | 387/594 |
| Msp I | 325 | 325 | 325 | 325 | 325 | 325 | 325 | 325 | 325 |
| Mun I | 598 | 534 | xxx | xxx | xxx | xxx | xxx | xxx | xxx |
| Nar I | 66 | 268 | 268 | xxx | xxx | xxx | xxx | 147/298 | xxx |
| Nci I | 326 | xxx | xxx | xxx | xxx | xxx | xxx | 326 | 326 |
| Nhe I | 194 | 194 | 194 | 194 | 194 | xxx | 194 | 194 | xxx |
| Nle III | 425/442 | 425/442 | 425/442 | 425/442 | 425/442 | xxx | 425/430/442 | 425/442 | 425 |
| Nle IV | 269/578 | 269/578 | 269/578 | 269/578 | 269/578 | xxx | 269/578 | 269/578 | 578 |
| Nru I | xxx | 65 | 65 | 65 | 65 | xxx | 65 | 65 | 65 |
| Nsp BII | 51/149 | 51/149/609 | 51/149/609 | 609 | 51/149 | 51 | 51/582/609 | 582/609 | 51/609 |
| Nsp HI | 425 | 425 | 425 | 425 | 425 | 425 | 425 | 425 | 425 |
| Ple I | 242/475 | 242/475 | 242/475 | 242/475 | 242/475 | 242/475 | 242/415 | 242/475 | 242/475 |
| Pvu I | xxx | xxx | xxx | xxx | 149 | xxx | xxx | 498 | xxx |
| Pvu II | 149 | 149 | 149 | xxx | 443 | xxx | 443 | 443 | 443 |
| Rsa I | 443 | 443 | 443 | 443 | 52 | 52 | 52/583 | 52 | 52 |
| Sac II | 52 | 52 | 52 | 52 | 547 | 547 | 547 | 495/547 | 547 |
| Sau 3al | 547 | 547 | 547 | 547/551 | 547 | xxx | 551 | xxx | xxx |
| Sau 96I | xxx | xxx | xxx | xxx | xxx | xxx | xxx | xxx | xxx |
| Scr FI | 326/378/428 | 378/428 | 378/428 | 326/378/428 | 306/326/428 | 378/428 | 326/378 | 326/378/428 | 326/378/428 |
| Sec I | 49/376/580 | 49/376/580 | 49/376/580 | 49/376/580 | 49/580 | multi(4) | 49/376/580 | 49/580 | 49/376/580 |
| Sfa NI | 367 | 367 | 367 | 367 | 367 | 367 | 30/367 | 367 | 367 |
| Sfc I | xxx | xxx | xxx | xxx | xxx | xxx | xxx | xxx | xxx |
| Sfi I | xxx | xxx | xxx | xxx | xxx | xxx | xxx | xxx | xxx |
| Sty I | xxx | xxx | xxx | xxx | xxx | 472 | xxx | xxx | xxx |
| Taq I | 535/550 | 535/550 | 535/550 | 550 | 535/550 | 550 | 535/550 535 | 535/550 | 535/550 |
| Tth 111I | 297 | 297 | 297 | xxx | 297 | 297 | xxx | 297 | 297 |
| Xba I | xxx | xxx | xxx | xxx | xxx | 464 | xxx | xxx | 464 |
| Xcm I | 461 | 461 | 461 | 461 | xxx | xxx | 461 | 461 | xxx |

| ENZYME | #13 | #14 | #15 | #16 | #17 | #18 | #19 | #20 | NADC-8 | NADC-9 | REF:V2332 |
|---|---|---|---|---|---|---|---|---|---|---|---|
| Hind PI | 431 | 431 | 127/431 | 431 | 108/118/431 | 373/431 | 431 | 431 | 108/118/431 | 108/118/431 | 431 |
| Hpa II | 325/609 | 325 | 325 | 325 | 325 | xxx | 325 | 325 | 325 | 325 | 325 |
| Hph I | 598 | 534 | 266 | xxx | 47/490 | xxx | 266/534 | 47/286/534 | 534 | 534 | xxx |
| Kas I | xxx | xxx | xxx | xxx | xxx | xxx | xxx | xxx | xxx | xxx | xxx |
| Mae I | 465/529 | 280/629 | 629 | 280/465/829 | 496 | 280 | 629 | 629 | 195/280 | 195/280 | 195 |
| Mae III | 308 | 308/540 | 308 | 308 | 547 | 308 | 308/540 | 308/540 | 308/540/593 | 308/540/593 | 308 |
| Mbo I | 547 | 547 | 495/547 | 547 | 425/453 | 324/425/453 | 547 | 425 | 547 | 547 | 547 |
| Mbo II | 324/425 | 425 | 425 | 425 | xxx | xxx | 425 | xxx | 425/453 | 425/453 | 453 |
| Mlu I | xxx | xxx | xxx | xxx | xxx | xxx | xxx | xxx | xxx | xxx | 436 |
| Mnl I | 333/523/564 | 523/564 | 523/564 | 523/564 | 282/523/564 | 523/584 | 523/564 | 486/523/564 | 282/523/564 | 282/523/564 | 282/523/564 |
| Msc I | xxx | xxx | xxx | xxx | xxx | xxx | xxx | xxx | xxx | xxx | xxx |
| Mse I | 594 | xxx | 566 | xxx | xxx | xxx | 594 | 594 | xxx | xxx | xxx |
| Msp I | 325/609 | 387/594 | 325 | 387/594 | 325 | xxx | 325 | 325 | 325 | 325 | 325 |
| Mun I | xxx | 325 | xxx | 325 | xxx | xxx | xxx | xxx | xxx | xxx | xxx |
| Nar I | xxx | xxx | xxx | xxx | xxx | xxx | xxx | xxx | 66 | 66 | xxx |
| Nci I | 326 | xxx | xxx | 326 | 326 | xxx | 326 | 326 | 326 | 326 | 326 |

TABLE II-continued

| Enzyme | | | | | | | | | | |
|---|---|---|---|---|---|---|---|---|---|---|
| Nhe I | xxx | xxx | xxx | xxx | xxx | xxx | xxx | 194 | 194 | 194 |
| Nle III | 425/442 | 425/442 | 425/442 | 425/442 | 425/442 | 425/442 | 425/442 | 425/442 | 425/442 | 425 |
| Nle IV | 578 | 578 | 578 | 269/578 | 578 | 578 | 578 | 269/578 | 269/578 | 269/578 |
| Nru I | 65 | 65 | 65 | 65 | 65 | 65 | 65 | xxx | xxx | 65 |
| Nsp BII | 51/582 | 51/582/609 | 51/609 | 51/582/609 | 51/609 | 51/609 | 51/609 | multi(4) | 51/149/582 | 51/149/609 |
| Nsp HI | 425 | 425 | 425 | 425 | 425 | 425 | 425 | 425 | 425 | 425 |
| Ple I | 475 | 242/475 | 242/475 | 242/475 | 242/475 | 242/475 | 242/475 | 242/475 | 242/475 | 242/475 |
| Pvu I | xxx | 498 | xxx | xxx | xxx | xxx | xxx | xxx | xxx | xxx |
| Pvu II | xxx | xxx | xxx | xxx | xxx | xxx | xxx | 149 | 149 | 149 |
| Rsa I | 185 | 443 | 443 | 443 | 443 | 443 | 443 | 443 | 443 | 443 |
| Sac II | 52/583 | 52 | 52 | 52/583 | 52 | 52 | 52 | 52/583 | 52/583 | 52 |
| Sau 3aI | 547 | 495/547 | 547 | 547 | 547 | 547 | 547 | 547 | 547 | 547 |
| Sau 96I |  | xxx | xxx | xxx | xxx | xxx | 53 | xxx | xxx | xxx |
| Scr FI | 326/378/428 | 98/378/428 | 326/378/428 | 326/428 | 326/428 | 326/428 | 326/428 | 378/428 | 326/378/426 | 326/378/428 |
| Sec I | 49/376/580 | 49/376/480 | 49/376/580 | 49/580 | 49/580 | 49/580 | 49/580 | 49/376/580 | 49/376/580 | 49/376/580 |
| Sfa NI | 367 | 367 | 367 | 367 | 367 | 367 | 367 | 367 | 367 | 367 |
| Sfc I | xxx | xxx | xxx | xxx | xxx | xxx | xxx | xxx | xxx | 144 |
| Sfi I | xxx | xxx | xxx | xxx | xxx | xxx | xxx | xxx | xxx | xxx |
| Sty I | 472 | xxx | 472 | 535/550 | 535/550 | 535/550 | 535/550 | 535/550 | 535/550 | 535/550 |
| Taq I | 535/550 | 535/550 | 535/550 | 535/550 | 535/550 | 535/550 | 535/550 | 535/550 | 529/535/550 | 297 |
| Tth 111I | 297 | 297 | 297 | 297 | 297 | xxx | xxx | 297 | 297 | xxx |
| Xba I | 464 | 464 | xxx | Xxx | xxx | xxx | xxx | xxx | xxx | xxx |
| Xcm I | xxx | 461 | 461 | 461 | 461 | 461 | 461 | 461 | 461 | 461 |

TABLE III

Restriction Enzyme Pattern after PRRSV Replication in vivo

| No. | Sample Type | Source | Duration of Infection | PRRSV Strain Exposure | Recovered |
|---|---|---|---|---|---|
| 1 | Lung-Lavage | Gilt | 7 wks | RespPRRS ® | RespPRRS ® |
| 2 | " | " | " | " | " |
| 3 | " | " | " | " | " |
| 4 | " | " | " | NADC-8 | NADC-8 |
| 5 | " | Pig-Pig | 8 + 3 | " | " |
| 6 | " | " | 8 + 3 | " | " |
| 7 | " | Gilt-Piglet | 8 + 5 | RespPRRS ® | RespPRRS ® |

REFERENCES

Balasuriya U B R, Maclachan N J, DeVries A A F, Rossitto P V, Rottier P J M (1995) Identification of a neutralization site in the major envelope glycoprotein ($G_L$) of equine arteritis virus. *Virology* 207:518–527.

Bautista E M, Goyal S M, Collins J E (1993) Serologic survey for Lelystad and VR-2332 strains of porcine respiratory and reproductive syndrome (PRRS) virus in US swine herds. *J Vet Diagn Invest* 5:621–614.

Conzelmann K K, Visser N. Van Woensel P, Thiel H J (1993) Molecular characterization of porcine reproductive and respiratory syndrome virus, a member of the Arteritis group. *Virology* 193:329–339.

De Vries A A F, Chirnside E D, Horzinek M C, Rottier P J M (1992) Structural proteins of equine arteritis virus. *J Virol* 6:6294–6303.

Godeny E K, Chen L, Kumar S N, Methven S L, Koonin E V, Brinton M A (1993) Complete genomic sequence and phylogenetic analysis of the lactate dehydrogenase-elevating virus (LDV). *Virology* 194:585–596.

Harty J T and Plagemann P G W (1988) Formalin inactivation of the lactate dehydrogenase-elevating virus reveals a major neutralizing epitope not recognized during natural infection. *J of Virol* 62:3210–3216.

Keffaber, K. K., (1989) Reproducting failure of unknown etiology. *Am. Asssoc. Swine Pract. News* 1:1–10.

Kim H S, Kwang J. Yoon I J, Joo H S, Frey M L (1993) Enhanced replication of porcine reproductive and respiratory syndrome (PRRS) virus in a homogeneous subpopulation of MA-104 cell line. *Arch Virol* 133:477–483.

Loula, T. (1991) Mystery pig disease. *Agri. Pract.* 12:23–33.

Meng X J, Paul P S, Halbur P G, (1994) Molecular cloning and nucleotide sequencing of the 3'-terminal genomic RNA of the porcine reproductive and respiratory syndrome virus. *J of Gen Virol* 75:1795–1801.

Meng X J, Paul P S, Halbur P G, Lum M A (1995) Phylogenetic analyses of the putative M (ORF 6) and N (ORF 7) genes of porcine reproductive and respiratory syndrome virus (PRRSV): implication for the existence of two genotypes of PRRSV in the U.S.A. and Europe. *Arch Virol* 140:745–755.

Meulenberg J J M, Hulst M M, De Meijer E J, Moonen P L J M, Den Besten A, De Kluyver E P, Wensvoort G, Moormann R J M (1993) Lelystad virus, the causative agent of porcine epidemic abortion and respiratory syndrome (PEARS), is related to LVD and EAV. *Virology* 192:62–72.

Meulenberg J J M, Petersen-Den Besten A, De Kluyver E P, Moormann R J M, Schaaper W M M, Wensvoort G (1995) Characterization of proteins encoded by ORFs 2 to 7 of Lelystad virus. *Virology* 206:155–163. Morozov I, Meng X J, Paul P S (1995) Sequence analysis of open reading frames (ORFs) 2 to 4 of a U.S. Isolate of porcine reproductive and respiratory syndrome virus. *Arch Virol* 140:1313–1319.

Persch S, Heinen E, Schmeer N, Ohlinger V F (1995) Antigenic variations between different PRRSV-isolates. In Proceedings of the Second International Symposium on Porcine Reproductive and Respiratory Syndrome (PRRS), Copenhagen, Denmark p. 7.

Plagemann P G and Moenning V (1992) Lactate dehydrogenase-elevating virus, equine arteritis virus and simian hemorrhagic fever virus, a new group of positive strand RNA virus. *Advances in Virus Research* 41:99–192.

Sambrook J, Fritsch E F, Maniatis T (1989) Molecular Cloning; A Laboratory Manual. Cold Spring Harbor Laboratory Press, Cold Springs Harbor, N.Y., 2nd ed.

Sanger F, Nicklen S, Coulson A R (1977) DNA sequencing with chain terminating inhibitors. *Proc Natl Acad Sci U.S.A.* 74:5463–5464.

Sellner L N, Coelen R J, Mackenzie J S (1992) A one-tube, one manipulation RT-PCR reaction for detection of Ross River virus. *J. Virol. Meth.*, 40:255–264 Snijder E J and Spaan W J M (1995).

Snijder E J and Spaan W J M (1995) The Coronaviruslike Superfamily. In The Coronaviridae. Ed. Siddell S G. New York: Plenum Press.

Tabor S and Richardson C C (1987) DNA sequence analysis with a modified bacteriophage T7DNA polymerase. *Proc Natl Acad Sci U.S.A.* 84:4767–4771.

Van Nieuwstadt A, Meulenberg J., Van Essen-Zandbergen A, Petersen-Den Besten A, Bende R, Moormann R, Wensvoort G (1995) Monoclonal antibodies specific for lelystad virus recognize two additional structural viral proteins, encoded by ORF3 and ORF4 of the viral genome. In Proceedings of the Second International Symposium on Porcine Reproductive and Respiratory Syndrome Virus (PRRS), Copenhagen, Denmark, p. 5.

Wensvoort G, Terpstra C, Pol J M A, ter Laak E A, Bloemraad M, de Kluyver E P, Kragten C, Van Buiten K L, den Besten A, Wagenaar F, Broekhuijsen J M, Moonen P L J M, Zetsstra T, de Boer E A, Tibben H J, de Jong M F, van't Veld P, Groenland G J R, van Gennep J A, Voets M T, Verheijden J H M, Braamskamp J (1991) Mystery swine disease in the Netherlands: the isolation of Lelystad virus. Vet. Q. 13:121–130.

Wensvoort G, de Kluyver E P, Luijtze E A, den Besten A, Harris L, Collins J E, Christianson W T, Chladek D (1992) Antigenic comparison of Lelystad virus and swine infertility and respiratory syndrome (SIRS) virus. *J of Vet Diag Invest* 4:134–138.

We claim:

1. A method for differentiating any one of a first North American strain of Porcine ReproductiVe and Respiratory Syndrome Virus (PRRSV) from any one of a second North American strain of said virus wherein said first and second North American strains are selected from the pool of all known North American strains of PRRSV comprising the steps:
   a. reverse transcribing and amplifying the ORP 5 region of said first strain to produce an amplified cDNA of said region;
   b. selecting from a matrix of ORF-5 restriction enzyme patterns for said known North American strains of PRRSV at least one restriction enzyme which yields a distinctive fragment profile from said cDNA as compared to a fragment profile of a corresponding cDNA from said second strain;
   c. cleaving the ORF 5 cDNA of said first strain with said at least one restriction enzyme;
   d. comparing the restriction enzyme fragment pattern resulting from step (c) with the restriction enzyme fragment pattern produced by digesting the cDNA from said second strain with the same enzyme used in step (c); and
   e. differentiating said first North American strain of PRRSV from said second North American strain of PRRSV based on the comparing in step (d).

2. The method of claim 1 wherein one of said strains is the vaccine strain of PRRSV characterized by an ORF 5 having SEQ ID NO:23.

3. The method as described in claim 2 wherein said restriction enzyme is selected from the group consisting of Mlu I and Sfc I.

4. The method as described in claim 1 wherein said restriction enzyme is selected from the group consisting of Mlu I, Sfc I, Hinc II and Sac II.

5. The method of claim 1 wherein said reverse transcribing and amplifying in step (a) is conducted using a universal set of primers for all combinations of first and second strains of PRRSV selected from the set of all North American strains of PRRSV.

6. A kit for differentiating a first North American strain of Porcine Reproductive and Respiratory Syndrome Virus (PRRSV) from a second North American strain of said virus comprising a pair of primers for amplifying ORP 5 cDNA from said first strain and at least one first restriction enzyme which yields a distinctive fragment profile for the ORF 5 cDNA from each of said first and second strains, wherein said first restriction enzyme is selected from the group consisting of MIu I and Sfc I.

7. The kit of claim 6 wherein said primers have the sequence of SEQ ID NO:25 and SEQ ID NO:26.

8. The kit of claim 6 further comprising at least one second restriction enzyme selected from the group consisting of Hinc II and Sac II.

9. The kit of claim 8 comprising three of said restriction enzymes.

* * * * *

SEQUENCE LISTING (1) GENERAL INFORMATION:

(iii) NUMBER OF SEQUENCES: 27

(2) INFORMATION FOR SEQ ID NO:1:

(i) SEQUENCE CHARACTERISTICS:
      (A) LENGTH: 603 base pairs
      (B) TYPE: nucleic acid
      (C) STRANDEDNESS: double
      (D) TOPOLOGY: linear (ii) MOLECULE TYPE: cDNA (iii) HYPOTHETICAL: NO (iv) ANTI-SENSE: NO (vi) ORIGINAL SOURCE:
      (A) ORGANISM: Porcine Reproductive and Respiratory Syndrome
         Virus
      (B) STRAIN: 46448(IA)

(xi) SEQUENCE DESCRIPTION: SEQ ID NO:1:

```
ATGTTGGGTA AATGCTTGAC CGCGGGCTGT TGCTCGCAAT TGCTTTTTTG GTGGTGTATC      60

GTGCCGTCTT GTTTTGTTGC GCTCGTCAGC GCCAACGGGA ACAGCAGCTC AAATTTACAG     120

CTGATTTACA ACTTGACGCT ATGTGAGCTG AATGGCACAG ATTGGCTAGC TAATAAATTT     180

GACTGGGCAG TGGAGTGTTT TGTCATTTTT CCCGTGTTGA CTCACATTGT CTCTTATGGT     240

GCCCTCACTA CTAGCCATTT CCTTGACACA GTCGGTCTGG TCACTGTGTC TACCGCCGGG     300

TTTGTTCACG GCGGTATGT TCTGAGTAGC ATCTACGCGG TCTGTGCCCT GGCTGCGTTG      360

ATTTGCTTCG TCATTAGGTT TGCGAAGAAT TGCATGTCCT GGCGCTACTC ATGTACCAGA     420

TATACCAACT TTCTTCTGGA CACTAAGGGC AGACTCTATC GTTGGCGGTC GCCTGTCATC     480

ATAGAGAAGA GGGGTAAAGT TGAGGTCGAA GGTCATCTGA TCGACCTCAA AAGAGTTGTG     540

CTTGATGGTT CCGTGGCAAC CCCTATAACC AAAGTTTCAG CAGAACAATG GGGTCGTCCT     600

TAG                                                                  603
```

(2) INFORMATION FOR SEQ ID NO:2:

(i) SEQUENCE CHARACTERISTICS:
      (A) LENGTH: 603 base pairs
      (B) TYPE: nucleic acid
      (C) STRANDEDNESS: double
      (D) TOPOLOGY: linear (ii) MOLECULE TYPE: cDNA (iii) HYPOTHETICAL: NO (iv) ANTI-SENSE: NO (vi) ORIGINAL SOURCE:
      (A) ORGANISM: Porcine Reproductive and Respiratory Syndrome
         Virus
      (B) STRAIN: 46907(KY)

(xi) SEQUENCE DESCRIPTION: SEQ ID NO:2:

```
ATGTTGGGGA AATGCTTGAC CGCGGGCTGT TGCTCGCGAT TGCTTTTTTT GTGGTGTATC      60

GTGCCGTCCT GTTTTGTTGC GCTCGTCAGC GCCAACAGCA ACAGCAGCTC CCATTTACAG     120

CTGATTTACA ACTTGACGCT ATGTGAGCTG AATGGCACAG ATTGGCTAGC TAGTAGATTT     180

GATTGGGCAG TGGAGTGTTT TGTCATCTTT CCTGTGCTGA CTCACATTGT CTCCTATGGC     240
```

```
GCCCTCACTA CCAGCCATTT CCTTGACACA GTCGGTCTGG CCACTGTGTC TACCGCCGGT      300

TTTCTTCGCG GGCGGTATGT TCTGAGTAGC ATCTACGCGG TCTGTGCCCT GGCTGCGTTG      360

TTTTGCTTCG TCATTAGATT GGCGAAGAAT TGCATGTCCT GGCGCTATTC ATGTACCAGA      420

TATACCAACT TTCTTCTGGA TACTAAGGGC AGACTCTATC GTTGGCGGTC GCCCGTCATC      480

ATAGAGAAAA AGGGTAAAGT TGAGGTCGAA GGTCATCTGA TCGACCTCAA GAGAGTTGTG      540

CTTGATGGTT CCGTGGCAAC CCCTGTAACC AGAGTTTCAG CGGAACAATG GGGTCGTCCT      600

TAG                                                                    603
```

(2) INFORMATION FOR SEQ ID NO:3:

(i) SEQUENCE CHARACTERISTICS:
        (A) LENGTH: 603 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Porcine Reproductive and Respiratory Syndrome
            Virus
        (B) STRAIN: 1205-D(MO)

(xi) SEQUENCE DESCRIPTION: SEQ ID NO:3:

```
ATGTTGGGGA AATGCTTGAC CGCGGGCTGT TGCTCGCGAT TGCTTTTTTT GTGGTGTATC       60

GTGCCGTCCT GTTTTGTTGC GCTCGTCAGC GCCAACAGCA ACAGCAGCTC TCATTTACAG      120

CTGATTTACA ACTTGACGCT ATGTGAGCTG AATGGCACAG ATTGGCTAGC TAATAAATTT      180

GATTGGGCAG TGGAATGTTT TGTCATCTTT CCTGTGCTGA CTCACATTGT CTCCTATGGC      240

GCCCTCACTA CCAGCCATTT CCTTGACACA TTCGGTCTGG CCACTGTGTC TACCGCCGGT      300

TTTCTTCACG GGCGGTATGT TCTGAGTAGC ATCTACGCGG TCTGTGCCCT GGCTGCGTTG      360

TTTTGCTTCG TCATTAGATT TGCGAAGAAT TGCATGTCCT GGCGCTATTC ATGTACCAGA      420

TATACCAACT TTCTTCTGGA TACTAAGGGC AGACTCTATC GTTGGCGGTC GCCCGTCATC      480

ATAGAGAAAA AGGGTAAAGT TGAGGTCGAA GGTCATCTGA TCGACCTCAA GAGAGTTGTG      540

CTTGATGGTT CCGTGGCAAC CCCTGTAACC AGAGTTTCAG CGGAACAATG GGGTCGTCCT      600

TAG                                                                    603
```

(2) INFORMATION FOR SEQ ID NO:4:

(i) SEQUENCE CHARACTERISTICS:
        (A) LENGTH: 603 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Porcine Reproductive and Respiratory Syndrome
            Virus
        (B) STRAIN: 10654(IA)

(xi) SEQUENCE DESCRIPTION: SEQ ID NO:4:

-continued

```
ATGTTGGGGA AATGCTTGAC CGCGGGCTGT TGCTCGCAAT TGCTTTTTTT GTGGTGTATC      60

GTGCCGTCTT GTCTTGTTGC GCTCGTCAGC GCCAACGGGA ACAGCAGCTC AAATTTACAG     120

CTGATTTACA ACTTGACGCT ATGTGAGCTG AATGGCACAG ATTGGCTAGC TAATAAATTT     180

GACTGGGCAG TGGAGTGTTT TGTCATTTTT CCCGTGTTGA CTCACATTGT CTCTTACGGT     240

GCCCTCACTA CTAGCCATTT CCTTGACACA GTCGGCCTGG TCACTGTGTC TACCGCCGGG     300

TTTGTTCACG GCGGTATGT TCTGAGTAGC ATCTACGCGG TCTGTGCCCT AGCTGCGTTG      360

ATTTGCTTCG TCATTAGGTT TGCGAAGAAT TGCATGTCCT GGCGCTACTC ATGTACCAGA     420

TATACTAACT TTCTTCTGGA CACTAAGGGC AGACTCTATC GTTGGCGGTC GCCCGTCATC     480

ATAGAGAAGA GGGGTAAAGT TGAGGTCGAA GGTCATCTGA TCGACCTCCA AGAGTTGTG     540

CTTGATGGTT CCGTGGCAAC CCCTATAACC AGAGTTTCAG CAGAACAATG GGGTCGTCCT     600

TAG                                                                  603
```

(2) INFORMATION FOR SEQ ID NO:5:

(i) SEQUENCE CHARACTERISTICS:
        (A) LENGTH: 603 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Porcine Reproductive and Respiratory Syndrome
            Virus
        (B) STRAIN: 30093-A(IL)

(xi) SEQUENCE DESCRIPTION: SEQ ID NO:5:

```
ATGTTGGGGA AATGCTTGAC CGCGGGCTGT TGCTCGCAAT TGCTTTTTTT GTGGTGTATC      60

GTGCCGTCTT GTCTTGTTGC GCTCGTCAGC GCCAACGGGA ACAGCAGCTC AAATTTACAG     120

CTGATTTACA ACTTGACGCT ATGTGAGCTG AATGGCACAG ATTGGCTAGC TAATAAATTT     180

GACTGGGCAG TGGAGTGTTT TGTCATTTTT CCCGTGTTGA CTCACATTGT CTCTTACGGT     240

GCCCTCACTA CTAGCCATTT CCTTGACACA GTCGGCCTGG TCACTGTGTC TACCGCCGGG     300

TTTGTTCACG GCGGTATGT TCTGAGTAGC ATCTACGCGG TCTGTGCCCT AGCTGCGTTG      360

ATTTGCTTCG TCATTAGGTT TGCGAAGAAT TGCATGTCCT GGCGCTACTC ATGTACCAGA     420

TATACTAACT TTCTTCTGGA CACTAAGGGC AGACTCTATC GTTGGCGGTC GCCCGTCATC     480

ATAGAGAAGA GGGGTAAAGT TGAGGTCGAA GGTCATCTGA TCGACCTCCA AGAGTTGTG     540

CTTGATGGTT CCGTGGCAAC CCCTATAACC AGAGTTTCAG CAGAACAATG GGGTCGTCCT     600

TAG                                                                  603
```

(2) INFORMATION FOR SEQ ID NO:6:

(i) SEQUENCE CHARACTERISTICS:
        (A) LENGTH: 603 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
    (A) ORGANISM: Porcine Reproductive and Respiratory Syndrome Virus
    (B) STRAIN: 34075(NE)

(xi) SEQUENCE DESCRIPTION: SEQ ID NO:6:

```
ATGTTGGGGA AATGCTTGAC CGCGGGCTGT TGCTTGCGAT TGCTTTCTTT GTGGTGTATC      60
GTGCCGTTCT TTTTTGCTGT GCTCGTCAAC GCCAACAGCA CCAGCAGCTC CCATTTGCAG     120
TTGATTTATA ACTTGACGCT ATGTGAGCTG AATGGCACAG ATTGGCTGGC TAATAAATTT     180
GATTGGGCAG TGGAGAGTTT TGTTATTTTT CCCGTGTTGA CTCACATTGT TTCCTATGGT     240
GCACTCACCA CCAGCCATTT CCTTGACACA GTCGGTCTAG TTACTGTGTC CACCGCCGGT     300
TTTCTTCACG GCGGTATGT CTTGAGTAGC ATCTACGCGG TCTGTGCCCT GGCTGCGTTG      360
GTTTGCTTCG GCATTAGGTT TGCGAAGAAC TGCATGTCCT GGCGCTACTC ATGTACCAGA     420
TATACCAACT TTCTTCTAGA CACCAAGGGC AGACTCTATC GTTGGCGGTC GCCTGTCATC     480
ATAGAGAAAA GGGGTAAGGT TGAGGTCGCA GGTCACCTAA TCGACCTCCA AAGAGTTGTG     540
CCTGATGGTT CCGTGGCCAC TCCTTTAACC AGAGTTTCAG CGGAACAATG GGGTCGTCCC     600
TAG                                                                  603
```

(2) INFORMATION FOR SEQ ID NO:7:

(i) SEQUENCE CHARACTERISTICS:
        (A) LENGTH: 603 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Porcine Reproductive and Respiratory Syndrome Virus
        (B) STRAIN: 49138(TX)

(xi) SEQUENCE DESCRIPTION: SEQ ID NO:7:

```
ATGTTGGGGA AATGCTTGAC CGCGGGCTGT TGCTCGCGAT TGCTTTCTTT GTGGTGTATC      60
GTGCCGTTCT GTTTTGCTGT GCTCGTCAAC GCCAACAGCA ACAGCAGCTC TCATTTTCAG     120
TTGATTTATA ACTTGACGCT ATGTGAGCTG AATGGCACAG ACTGGCTGGC TAACAAATTT     180
GATTGGGCAG TGGAGACTTT TGTCATCTTT CCCGTGTTGA CTCACATTGT TTCCTATGGT     240
GCACTCACCA CCAGCCATTT CCTTGACACA GTTGGTCTGG TTACTGTGTC CACCGCCGGG     300
TTTTATCACG GCGGTATGT CTTGAGTAGC ATCTACGCGG TCTGTGCTCT GGCTGCGTTG      360
ATTTGCTTCG TCATTAGGTT TGCGAAGAAC TGCATGTCCT GGCGCTACTC ATGTACCAGA     420
TATACCAACT TCCTCCTAGA TACTAAGGGC AGACTCTATC GTTGGCGGTC GCCTGTTATC     480
ATAGAGAAAG GGGGTAAGGT TGAGGTCGAA GGCCACCTGA TCGACCTCCA AAGAGTTGTG     540
CTTGATGGTT CCGTGGCAAC TCCTTTAACC AGAGTTTCAG CAGAACAATG GGGTCGTCCC     600
TAG                                                                  603
```

(2) INFORMATION FOR SEQ ID NO:8:

(i) SEQUENCE CHARACTERISTICS:
        (A) LENGTH: 603 base pairs (B) TYPE: nucleic acid
(C) STRANDEDNESS: double
(D) TOPOLOGY: linear (ii) MOLECULE TYPE: cDNA (iii) HYPOTHETICAL: NO (iv) ANTI-SENSE: NO (vi) ORIGINAL SOURCE:
(A) ORGANISM: Porcine Reproductive and Respiratory Virus
(B) STRAIN: 5556(MI)

(xi) SEQUENCE DESCRIPTION: SEQ ID NO:8:

```
ATGTTGGTGA GATGCTTGAC CGCGGGCTGT TGCTCGCGAT T

TAG 603

(2) INFORMATION FOR SEQ ID NO:10:

(i) SEQUENCE CHARACTERISTICS:
        (A) LENGTH: 603 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Porcine Reproductive and Respiratory Syndrome
            Virus
        (B) STRAIN: 5591(NC)

(xi) SEQUENCE DESCRIPTION: SEQ ID NO:10:

```
ATGTTGGGGA AATGCTTGAC CGCGGATTGT TGCTCGCGAT TGCTTTTTTT GTGGTGTATC      60

GTGCCGTTCT GGTTTGCTGT GCTCGGCAAC GCCAACAGCA CCAGCAGCTC TCACTTACAG     120

TTGATTTATA ACTTGACGCT ATGTGAGCTG AATGGCACAG ATTGGTTGGC TAACAAATTT     180

GATTGGGCAG TGGAGAGTTT TGTTATTTTT CCCGTGTTGA CTCACATTGT TTCCTATGGT     240

GCACTCACCA CCAGCCATTT CCTTGACACA GTCGGTCTGG TTACTGTGTC TACCGCCGGG     300

TTTTGTCACG GCGGTATGT CTTGAGTAGC ATCTACGCGG TCTGTGCTCT GGCCGCGTTG      360

ATTTGTTTCG TCATCAGGTT TGCGAAGAAC TGCATGTCCT GGCGCTACTC ATGTACCAGA     420

TATACCAACT TCCTTCTGGA CACTAAGGGC AGACTCTATC GTTGGCGATC GCCTGTCATC     480

ATAGAGAAAG GGGTAAGGT TGAGGTCGAA GGCCATCTGA TCGACCTCCA AAGAGTTGTG      540

CTTGATGGTT CCGTGGCAAC CCCTTTAACC AGAGTTTCAG CGGAACAATG GGGTCGTCCC     600

TAG                                                                   603
```

(2) INFORMATION FOR SEQ ID NO:11:

(i) SEQUENCE CHARACTERISTICS:
        (A) LENGTH: 603 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Porcine Reproductive and Respiratory Syndrome
            Virus
        (B) STRAIN: 14622(AR)

(xi) SEQUENCE DESCRIPTION: SEQ ID NO:11:

```
ATGTTGGGGA AATGCTTGAC CGCGGGCTGT TGCTCGCGAT TGCTTTCTTT GTGGTTTATC      60

GTGCCGTTCT GTTTTGCTGT GCTCGTCAAC GCCAACAGCA ACAGCAGCTC TCATTCACAG     120

TTGATTTATA ACCTGACGCT ATGTGAGCTG AATGGCACAG ATTGGCTGGC TAATAAATTT     180

GATTGGGCAG TGGAGAGTTT TGTCATCTTT CCTGTGCTGA CTCACATTGT CTCTTATAGT     240

GCCCTCACTA CCAGCCATTT CCTTGACACA GTCGGTCTGG CCACTGTGTC TACCGCCGGA     300

TTTGTTCACG GCGGGTATGT TCTGAGTAGC ATCTACGCGG TCTGCGCCCT GGCTGCGTTG     360
```

```
ATTTGCTTCA TCATCAGGTT TGCGAAGAAT TGCATGTCCT GGCGCTACTC TTGTACCAGA      420

TATACCAACT TTCTTCTGGA CACTAAGGGC AGACTCTATC GTTGGCGGTC GCCCGTCATC      480

ATAGAGAAAA GGGGCAAAGT TGAGGTCGAA GGTCATCTGA TCGACCTCAA GAGAGTTGTG      540

CTTGATGGTT CCGCGGCAAC CCCTGTAACC AAAGTTTCAG CGGAACAATG GGGTCATCCT      600

TAG                                                                   603
```

(2) INFORMATION FOR SEQ ID NO:12:

(i) SEQUENCE CHARACTERISTICS:
        (A) LENGTH: 603 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Porcine Reproductive and Respiratory Syndrome
            Virus
        (B) STRAIN: 19950-E(MN)

(xi) SEQUENCE DESCRIPTION: SEQ ID NO:12:

```
ATGTTGGGGA AATGCTTGAC CGCGGGCTGT TGCTCGCGAT TGCTTTCTTT GTGGTGTATC       60

GTGCCGTTCT GTTTTGCTGT GCTCGTCAAC GCCAACAGCA GCAGCAGCTC TCATTTTCAG      120

TTGATTTATA ACTTGACGCT ATGTGAGCTG AATGGCACAG ATTGGCTGGC TGAGAAATTT      180

GATTGGGCGG TGGAAAGTTT TGTCATTTTT CCCGTGTTGA CTCACATTGT TTCCTATGGT      240

GCACTCACTA CTAGCCATTT TCTTGACACA GTCGGTCTGG TTACTGTGTC TACCGCCGGG      300

TTTTGGCACG GCGGTATGT CTTGAGCAGC ATCTACGCGG TCTGTGCCCT GGCTGCGTTA      360

ATTTGCTTTG TCATTAGGCT TGCGAAGAAC TGCATGTCCT GGCGCTACTC TTGTACCAGA      420

TATACTAACT TCCTTCTAGA CACTAAGGGC AGACTCTATC GTTGGCGGTC GCCCGTTATC      480

ATAGAGAAAG GGGGTAAGGT TGAGGTCGAA GGTCACCTGA TCGACCTCAA AAGAGTTGTG      540

CTTGATGGTT CCGTGGCAAC CCCTTTAACC AGAGTTTCAG CGGAACAATG GGGTCGTCCC      600

TAG                                                                   603
```

(2) INFORMATION FOR SEQ ID NO:13:

(i) SEQUENCE CHARACTERISTICS:
        (A) LENGTH: 603 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Porcine Reproductive and Respiratory Syndrome
            Virus
        (B) STRAIN: 26948-2(VA)

(xi) SEQUENCE DESCRIPTION: SEQ ID NO:13:

```
ATGTTGGGGA AATGCTTGAC CGCGGGCTGT TGCTCGCGAT TGCCTTTTTT GTGGTGTATC       60

GTGCCGTTCT GTTTTGGTGT GCTCGTCAAC GCCAACAGCA GCAGCAGCTC TCATTTTCAG      120
```

```
TTGATTTATA ACTTGACGCT ATGTGAGCTG AATGGTACAG ATTGGCTGGC AGGAAAATTT        180

GATTGGGCAG TGGAGAGTTT TGTCATTTTT CCCGTGCTGA CCCACATTGT TTCCTATGGT        240

GCACTTACTA CCAGCCATTT CCTTGACACA GTCGGTCTGG TTACCGTGTC TACCGCCGGG        300

TTTCTTCACG GGAGGTATGT CCTGAGTAGC ATCTACGCGG TCTGTGCCCT GGCTGCGTTG        360

ATTTGCTTCG TCATTAGGCT TGCGAAGAAC TGCATGTCCT GGCGCTACTC ATGCACCAGA        420

TATACCAACT TCCTTCTAGA CACTAAGGGC AGACTCTATC GTTGGCGGTC GCCTGTTATC        480

ATAGAAAAAA AAGGTAAGGT TGAGGTCGAA GGTCATCTGA TCGACCTCAA AAGAGTTGTG        540

CTTGATGGTT CCGCGGCAAC TCCTTTAACC AGAGTTTCAC CGGAACAATG GGGTCGTCCC        600

TAG                                                                      603

(2) INFORMATION FOR SEQ ID NO:14:

(i) SEQUENCE CHARACTERISTICS:
        (A) LENGTH: 603 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Porcine Reproductive and Respiratory Syndrome
            Virus
        (B) STRAIN: 41572-2(NE)

(xi) SEQUENCE DESCRIPTION: SEQ ID NO:14:

ATGTTGGGGA AATGCTTGAC CGCGGGCTGT TGCTCGCGAT TGCTTTCTTT GTGGTGTATC         60

GTGCCGTTCT GGTTTGCTGT GCTCGTCAAC GCCAGCAGCA ACAGCAGCTC TCATTTTCAG        120

TTGATTTATA ACTTGACGCT ATGTGAGCTG AATGGCACAG ATTGGCTGGC TAATAAATTT        180

GATTGGGCAG TGGAGAGTTT TGTCATCTTT CCTGTGTTGA CTCACATTGT TTCCTATGGT        240

GCACTCACTA CTAGCCATTT CCTTGACACA GTCGGTCTGG TTACTGTGTC CACCGCCGGT        300

TTTTTTCACG GCGGTATGT CTTGAGCAGC ATCTACGCGG TCTGTGCCCT GGCTGCGTTA        360

ATTTGCTTTG TCATTAGGCT TGCGAAGAAC TGCATGTCCT GGCGCTACTC ATGTACCAGA        420

TATACCAACT TCCTTCTGGA CACCAAGGGC AGACTCTATC GTTGGCGGTC GCCCGTTATC        480

ATAGAGAAAA GGGGTAAGGT TGAGGTCGAA GGTCACCTGA TCGACCTCAA AAGAGTTGTG        540

CTTGATGGTT CCGCGGCTAC CCCTTTAACC AGAGTTTCAG CGGAACAATG GGGTCGTCCC        600

TAG                                                                      603

(2) INFORMATION FOR SEQ ID NO:15:

(i) SEQUENCE CHARACTERISTICS:
        (A) LENGTH: 603 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Porcine Reproductive and Respiratory Syndrome
            Virus
```

(B) STRAIN: 42928(IL)

(xi) SEQUENCE DESCRIPTION: SEQ ID NO:15:

```
ATGTTGGGGA AATGCTTGAC CGCGGGCTGT TGCTCGCGAT TGCTTTCTTT GTGGTGTATC      60

GTGCCGTCCT GGTTTGCTGT GCTCGTCAAC GCCAACAGCG CCAGCAGCTC TCATTTGCAG     120

TTGATTTATA ACTTGACGCT ATGTGAGCTG AATGGCACAG ATTGGTTGGC TGACAAGTTT     180

GATTGGGCAG TGGAGACTTT TGTTCTTTAT CCCGTGTTGA CTCACATTGT TTCCTATGGT     240

GCACTCACCA CCAGCCATTT CCTTGACACA GTCGGTCTGG TTACTGTGTC CACCGCCGGT     300

TTTGTTCACG GGCGGTATGT CTTGAGTAGC ATCTACGCGG TCTGTGCCCT GGCTGCGTTG     360

AGTTGTTTTG TCATCAGGTT TGTGAAGAAC TGCATGTCCT GGCGCTACTC ATGTACCAGA     420

TATACCAACT TCCTTCTGGA CACTAAGGGC AGACTCTATC GTTGGCGATC GCCTGTCATC     480

ATAGAGAAAG GGGGTAAGGT TGAGGTCGAA GGCCATCTGA TCGACCTCAA AAGAGTTGTG     540

CTTGATGGTT CCGTGGCAAC CCCTTTAACC AGAGTTTCAG CGGAACGATG GGGTCGTCCC     600

TAG                                                                  603
```

(2) INFORMATION FOR SEQ ID NO:16:

(i) SEQUENCE CHARACTERISTICS:
        (A) LENGTH: 603 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Porcine Reproductive and Respiratory Syndrome
            Virus
        (B) STRAIN: 32983-LG(NC)

(xi) SEQUENCE DESCRIPTION: SEQ ID NO:16:

```
ATGTTGGGGA AATGCTTGAC CGCGGGCTGC TGCTCGCGAT TGCTTTCTTT GTGGTGTATC      60

GTGCCGTTCT GTTTTGCTGT GCTCGTCAAC GCCAACAGCA GCAGCAGCTC TCATTTTCAG     120

TTGATTTATA ACTTGACGCT ATGTGAGCTG AATGGCACAG ATTGGCTGGC TGGGGAATTT     180

GATTGGGCGG TGGAAAGTTT TGTCATTTTT CCCGTGTTGA CTCACATTGT TTCCTATGGT     240

GCACTCACTA CTAGCCATTT TCTTGACACA GTCGGTCTGG TTACTGTGTC TACCGCCGGG     300

TTTTTGCACG GGCGGTATGT CTTGAGCAGC ATCTACGCGG TTTGTGCCCT GGCTGCGTTA     360

ATTTGCTTTG TCATTAGGCT TGCGAAGAAC TGCATGTCCT GGCGCTACTC ATGTACCAGA     420

TATACTAACT TCCTTCTAGA CACTAAGGGC AGACTCTATC GTTGGCGGTC GCCCGTTATC     480

ATAGAGAAAG GGGGTAAGGT TGAGGTCGAA GGTCATCTGA TCGACCTCAA AAGAGTTGTG     540

CTTGATGGTT CCGTGGCAAC CCCTTTAACC AGAGTTTCAG CGGAACAATG GGGTCGTCCC     600

TAG                                                                  603
```

(2) INFORMATION FOR SEQ ID NO:17:

(i) SEQUENCE CHARACTERISTICS:
        (A) LENGTH: 603 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
    (A) ORGANISM: Porcine Reproductive and Respiratory Syndrome Virus
    (B) STRAIN: 30352-3(MI)

(xi) SEQUENCE DESCRIPTION: SEQ ID NO:17:

```
ATGTTGGTGA AATGCTTGAC CGCGGGCTGT TGCTCGCGAT TGCTTTTTTT GTGGTGTATC      60
GTGCCGTCCT GTTTTGTTGC GCTCGTCAGC GCCAACGCCA ACAGCAGCTC CCATTCACAG     120
TTGATTTACA ACCTGACGCT ATGTGAGCTG AATGGCACAG ATTGGCTGTC TAATAAATTT     180
GATTGGGCAG TGGAGTGTTT TGTCATCTTT CCTGTGCTGA CTCACATTGT CTCCTATGGT     240
GCCCTCACTA CCAGCCATTT CCTTGACACA GTCGGTCTGG CCGTTGTGTC TACCGCCGGG     300
TTTGTTCACG GCGGTATGT TCTGAGTAGC ATCTACGCGG TCTGTGCCCT TGCTGCGTTG      360
ATTTGCTTCG TCATTAGATT TGCGAAGAAT TGCATGTCCT GGCGCTACTC ATGTACCAGA     420
TATACCAACT TTCTTCTGGA CACTAAGGGC AGACTCTATC GTTGGCGGTC ACCTGTCATC     480
ATAGAGAAAA GGGGTAAAGT TGAGGTCGAA GGTAATCTGA TCGACCTCAA GAGAGTTGTG     540
CTTGATGGTT CCGCGGCAAC CCCTATAACC AAAGTTTCAG CGGAACAATG GGGTCATCCT     600
TAG                                                                   603
```

(2) INFORMATION FOR SEQ ID NO:18:

(i) SEQUENCE CHARACTERISTICS:
    (A) LENGTH: 603 base pairs
    (B) TYPE: nucleic acid
    (C) STRANDEDNESS: double
    (D) TOPOLOGY: linear (ii) MOLECULE TYPE: cDNA (iii) HYPOTHETICAL: NO (iv) ANTI-SENSE: NO (vi) ORIGINAL SOURCE:
    (A) ORGANISM: Porcine Reproductive and Respiratory Syndrome Virus
    (B) STRAIN: 47324-2(CAN)

(xi) SEQUENCE DESCRIPTION: SEQ ID NO:18:

```
ATGTTGGGGA AATGCTTGAC CGCGGGCTGT TGCTCGCGAT TGCTTTTTTT GTGGTGTATC      60
GTGCCGTCCT GTTTTGTTGT GCTCGTCAAC GCCAACAACA GAAGCAGCTC CCATTTTCAG     120
TTGATTTATA ACTTGACGCT ATGTGAGCTG AATGGCACAG ATTGGCTGGC TGATAAATTT     180
GATTGGGCAG TGGAGAGTTT TGTCATCTTT CCCGTTTTGA CTCACATTGT TTCCTATGGT     240
GCCCTAACCA CTAGCCATTT TCTTGACACA GTTGGTCTGG TTACTGTGTC TACCGCTGGT     300
TTTCTTCACG GCGGTATGT TCTGAGTAGC ATCTACGCGG TCTGCGCCCT GGCTGCGTTG      360
ATTTGCTTTG TCATTAGGTT CGTGAAGAAC TGCATGTCCT GGCGCTACTC ATGTACCAGA     420
CATACCAACT TTCTTCTGGA TACCAAGGGC AGACTCTATC GTTGGCGGTC GCCCGTCATC     480
ATAGAGAAAG GGGGTAAAGT TGAGGTCGAA GGTCATCTCA TCGACCTCAA GAGAGTTGTG     540
CTTGATGGTT CCGCGGCAAC CCCTATAACC AGAGTTTCAG CGGAACAATG GGGTCGTCCT     600
TAG                                                                   603
```

(2) INFORMATION FOR SEQ ID NO:19:

(i) SEQUENCE CHARACTERISTICS:
    (A) LENGTH: 603 base pairs
    (B) TYPE: nucleic acid
    (C) STRANDEDNESS: double
    (D) TOPOLOGY: linear (ii) MOLECULE TYPE: cDNA (iii) HYPOTHETICAL: NO (iv) ANTI-SENSE: NO (vi) ORIGINAL SOURCE:
    (A) ORGANISM: Porcine Reproductive and Respiratory Syndrome
        Virus
    (B) STRAIN: 18310-A(PA)

(xi) SEQUENCE DESCRIPTION: SEQ ID NO:19:

```
ATGTTGGGGA AATGCTTGAC CGCGGGCTGT TGCTCGCGAT TGCTTTCTTT GTGGTGTATC      60
GTGCCGTTCT GTTTTGCTGT GCTCGTCAAC GCCAACAGCA ACAGCAGCTC TCATTTTCAG     120
TTGATTTATA ACTTGACGCT ATGTGAGCTG AATGGCACAG ACTGGCTGGC TAACAAATTT     180
GATTGGGCAG TGGAGACTTT TGTCATTTTT CCCGTATTGA CTCACATTGT TTCCTATGGT     240
GCACTCACCA CCAGCCATTT CCTTGACACA GTTGGTCTGG TTACTGTGTC CACCGCCGGG     300
TTTTATCACG GGCGGTATGT CTTGAGTAGC ATCTATGCGG TCTGTGCTCT GGCTGCGTTG     360
TTTTGCTTCG TCATTAGGCT TGCGAAGAAC TGCATGTCCT GGCGCTACTC TTGTACCAGA     420
TATACCAACT TCCTTCTGGA CACTAAGGGC AGACTCTATC GTTGGCGGTC GCCCGTTATT     480
ATAGAGAAAG GGGGTAAGGT TGAGGTCGAA GGTCACCTGA TCGACCTCAA AGAGTTGTG      540
CTTGATGGTT CCGTGGCAAC CCCTTTAACC AGAGTTTCAG CGGAACAATG GGGTCGTCTC     600
TAG                                                                   603
```

(2) INFORMATION FOR SEQ ID NO:20:

(i) SEQUENCE CHARACTERISTICS:
    (A) LENGTH: 603 base pairs
    (B) TYPE: nucleic acid
    (C) STRANDEDNESS: double
    (D) TOPOLOGY: linear (ii) MOLECULE TYPE: cDNA (iii) HYPOTHETICAL: NO (iv) ANTI-SENSE: NO (vi) ORIGINAL SOURCE:
    (A) ORGANISM: Porcine Reproductive and Respiratory Syndrome
        Virus
    (B) STRAIN: 24901(GUA)

(xi) SEQUENCE DESCRIPTION: SEQ ID NO:20:

```
ATGTTGGTGA AATGCTTGAC CGCGGGCCGT TGCTCGCGAT TGCCTTTTTT GTGGTGTATC      60
GTGCCGTTCT GTTTTGCTGT GCTCGTCAAC GCCAACAGCA GCAGCAGCTC TCATTTTCAG     120
TTGATTTATA ACTTGACGCT ATGTGAGCTG AATGGCACAG ATTGGCTGGC TGACAAATTT     180
GATTGGGCAG TAGAGACTTT TGTCATCTTT CCCGTGTTGA CTCACATTGT TTCCTATGGT     240
GCACTCACCA CCAGCCATTT CCTTGACACA GTTGGTCTGG TTACTGTGTC CACCGCCGGG     300
TTTTATCACG GGCGGTATGT CTTGAGTAGC ATCTACGCGG TCTGTGCTCT GGCTGCGTTG     360
ATTTGCTTCG TCATTAGGCT TGCGAAGAAC TGCATGTCCT GGCGCTACTC TTGTACCAGA     420
TATACCAACT TCCTTCTGGA CACTAAGGGC AGACTCTATC GTTGGAGGTC GCCCGTTATC     480
```

```
ATAGAGAAAG GGGGTAAGGT TGAGGTCGAA GGTCACCTGA TCGACCTCCA AAGAGTTGTG    540

CTTGATGGTT CCGTGGCAAC CCCTTTAACC AGAGTTTCAG CGGAACAATG GGGTCGTCCC    600

TAG                                                                  603
```

(2) INFORMATION FOR SEQ ID NO:21:

(i) SEQUENCE CHARACTERISTICS:
        (A) LENGTH: 603 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Porcine Reproductive and Respiratory Syndrome
            Virus
        (B) STRAIN: NADC-8(IA)

(xi) SEQUENCE DESCRIPTION: SEQ ID NO:21:

```
ATGTTGGGGA AATGCTTGAC CGCGGGCTGT TGCTCGCAAT TGCTTTTTTT GTGGTGTATC     60

GTGCCGTCTT GTTTTGTTGC GCTCGTCAGC GCCAACAGCA ACAGCAGCTC AAATTTACAG    120

CTGATTTACA ACTTGACGCT ATGTGAGCTG AATGGCACAG ATTGGCTAGC TAATAAATTT    180

GACTGGGCAG TGGAGTGTTT TGTCATCTTT CCTGTGTTGA CTCACATTGT CTCTTATGGT    240

GCCCTCACTA CTAGCCATTT CCTTGACACA GTCGGTCTGG TCACTGTGTC CACCGCCGGA    300

TTTTTTCACG GCGGTATGT TCTGAGTAGC ATCTACGCGG TCTGTGCCCT GGCTGCGTTG     360

ATTTGCTTCG TCATTAGGCT TGCGAAGAAT TGCATGTCCT GGCGCTACTC ATGTACCAGA    420

TATACCAACT TTCTTCTGGA CACTAAGGGC AGACTCTATC GTTGGCGGTC GCCTGTCATC    480

ATAGAGAAAA GGGGCAAAGT TGAGGTCGAA GGTCACCTGA TCGACCTCAA AAGAGTTGTG    540

CTTGATGGTT CCGCGGCAAC CCCTGTAACC AGAGTTTCAG CGGAACAATG GGGTCGTCCT    600

TAG                                                                  603
```

(2) INFORMATION FOR SEQ ID NO:22:

(i) SEQUENCE CHARACTERISTICS:
        (A) LENGTH: 603 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Porcine Reproductive and Respiratory Syndrome
            Virus
        (B) STRAIN: NADC-9(IA)

(xi) SEQUENCE DESCRIPTION: SEQ ID NO:22:

```
ATGTTGGTGA AATGCTTGAC CGCGGGCTGT TGCTCGCAAT TGCTTTTTTT GTGGTGTATC     60

GTGTCGTCCT GTTTTGTAGC GCTCGTCAGC GCCAACACGA CCAGCAGCTC AAATTTACAG    120

CTGATTTACA ACTTGACGCT ATGTGAGCTG AATGGCACAG ATTGGCTAGC TAATAAATTT    180

GACTGGGCAG TGGAGTGTTT TGTCATTTTT CCTGTGTTGA CTCACATTGT CTCTTATGGT    240
```

```
GCCCTCACTA CTAGCCATTT CCTTGACACA GTCGGTCTGG TCACTGTGTC CACCGCCGGG      300

TTTGTTCACG GGCGGTATGT TCTGAGTAGC ATCTACGCGG TCTGTGCCCT GGCTGCGTTG      360

ATTTGCTTCG TCATTAGGCT TGCGAAGAAC TGCATGTCCT GGCGCTACTC ATGTACCAGA      420

TATACCAACT TTCTTCTGGA CACTAAGGGC AGACTCTATC GTTGGCGGTC GCCTGTCATC      480

GTAGAGAAAA GGGGCAAGGT CGAGGTCGAA GGTCACCTGA TCGACCTCAA AAGAGTTGTG      540

CTTGATGGTT CCGCGGCAAC TCCTGTAACC AGAATTTCAT CAGAACAATG GGGTCGTCCT      600

TAG                                                                   603

(2) INFORMATION FOR SEQ ID NO:23:

(i) SEQUENCE CHARACTERISTICS:
        (A) LENGTH: 603 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Porcine Reproductive and Respiratory Syndrome
            Virus
        (B) STRAIN: RespPRRS (xi) SEQUENCE DESCRIPTION: SEQ ID NO:23:

ATGTTGGAGA AATGCTTGAC CGCGGGCTGT TGCTCGCAAT TGCTTTCTTT GTGGTGTATC       60

GTGCCGTTCT GTTTTGCTGT GCTCGCCAAC GCCAGCAACG ACAGCAGCTC CCATCTACAG      120

CTGATTTACA ACTTGACGCT ATGTGAGCTG AATGGCACAG ATTGGCTAGC TAACAAATTT      180

GATTGGGCAG TGGAGAGTTT TGTCATCTTT CCCGTTTTGA CTCACATTGT CTCCTATGGT      240

GCCCTCACTA CCAGCCATTT CCTTGACACA GTCGCTTTAG TCACTGTGTC TACCGCCGGG      300

TTTGTTCACG GCGGTATGT CCTAAGTAGC ATCTACGCGG TCTGTGCCCT GGCTGCGTTG      360

ACTTGCTTCG TCATTAGGTT TGCAAAGAAT TGCATGTCCT GGCGCTACGC GTGTACCAGA      420

TATACCAACT TTCTTCTGGA CACTAAGGGC GGACTCTATC GTTGGCGGTC GCCTGTCATC      480

ATAGAGAAAA GGGGCAAAGT TGAGGTCGAA GGTCATCTGA TCGACCTCAA AAGAGTTGTG      540

CTTGATGGTT CCGTGGCAAC CCCTATAACC AGAGTTTCAG CGGAACAATG GGGTCGTCCT      600

TAG                                                                   603

(2) INFORMATION FOR SEQ ID NO:24:

(i) SEQUENCE CHARACTERISTICS:
        (A) LENGTH: 603 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Porcine Reproductive and Respiratory Syndrome
            Virus
        (B) STRAIN: 2332(MN)

(xi) SEQUENCE DESCRIPTION: SEQ ID NO:24:
```

```
ATGTTGGAGA AATGCTTGAC CGCGGGCTGT TGCTCGCGAT TGCTTTCTTT GTGGTGTATC        60

GTGCCGTTCT GTTTTGCTGT GCTCGCCAAC GCCAGCAACG ACAGCAGCTC CCATCTACAG       120

CTGATTTACA ACTTGACGCT ATGTGAGCTG AATGGCACAG ATTGGCTAGC TAACAAATTT       180

GATTGGGCAG TGGAGAGTTT TGTCATCTTT CCCGTTTTGA CTCACATTGT CTCCTATGGT       240

GCCCTCACTA CCAGCCATTT CCTTGACACA GTCGCTTTAG TCACTGTGTC TACCGCCGGG       300

TTTGTTCACG GCGGTATGT CCTAAGTAGC ATCTACGCGG TCTGTGCCCT GGCTGCGTTG       360

ACTTGCTTCG TCATTAGGTT TGCAAAGAAT TGCATGTCCT GGCGCTACGC GTGTACCAGA       420

TATACCAACT TTCTTCTGGA CACTAAGGGC AGACTCTATC GTTGGCGGTC GCCTGTCATC       480

ATAGAGAAAA GGGGCAAAGT TGAGGTCGAA GGTCATCTGA TCGACCTCAA AAGAGTTGTG       540

CTTGATGGTT CCGTGGCAAC CCCTATAACC AGAGTTTCAG CGGAACAATG GGGTCGTCCT       600

TAG                                                                     603

(2) INFORMATION FOR SEQ ID NO:25:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: YES (iv) ANTI-SENSE: NO (vi) ORIGINAL SOURCE:
        (A) ORGANISM: Porcine Reproductive and Respiratory Syndrome
            Virus (xi) SEQUENCE DESCRIPTION: SEQ ID NO:25:

CCATTCTGTT GGCAATTTGA                                                    20

(2) INFORMATION FOR SEQ ID NO:26:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (vi) ORIGINAL SOURCE:
        (A) ORGANISM: Porcine Reproductive and Respiratory Syndrome
            Virus (xi) SEQUENCE DESCRIPTION: SEQ ID NO:26:

GGCATATATC ATCACTGGCG                                                    20

(2) INFORMATION FOR SEQ ID NO:27:

(i) SEQUENCE CHARACTERISTICS:
        (A) LENGTH: 716 base pairs
        (B) TYPE: nucleic acid
        (C) STRANDEDNESS: double
        (D) TOPOLOGY: linear (ii) MOLECULE TYPE: cDNA (iii) HYPOTHETICAL: NO
```

(iv) ANTI-SENSE: NO (vi) ORIGINAL SOURCE:
      (A) ORGANISM: Porcine Reproductive and Respiratory Syndrome
          Virus
      (B) STRAIN: RespPRRS (xi) SEQUENCE DESCRIPTION: SEQ ID NO:27:

```
CCATTCTGTT GGCAATTTGA ATGTTTAAGT ATGTTGGAGA AATGCTTGAC CGCGGGCTGT    60

TGCTCGCAAT TGCTTTCTTT GTGGTGTATC GTGCCGTTCT GTTTTGCTGT GCTCGCCAAC   120

GCCAGCAACG ACAGCAGCTC CCATCTACAG CTGATTTACA ACTTGACGCT ATGTGAGCTG   180

AATGGCACAG ATTGGCTAGC TAACAAATTT GATTGGGCAG TGGAGAGTTT TGTCATCTTT   240

CCCGTTTTGA CTCACATTGT CTCCTATGGT GCCCTCACTA CCAGCCATTT CCTTGACACA   300

GTCGCTTTAG TCACTGTGTC TACCGCCGGG TTTGTTCACG GGCGGTATGT CCTAAGTAGC   360

ATCTACGCGG TCTGTGCCCT GGCTGCGTTG ACTTGCTTCG TCATTAGGTT TGCAAAGAAT   420

TGCATGTCCT GGCGCTACGC GTGTACCAGA TATACCAACT TTCTTCTGGA CACTAAGGGC   480

GGACTCTATC GTTGGCGGTC GCCTGTCATC ATAGAGAAAA GGGGCAAAGT TGAGGTCGAA   540

GGTCATCTGA TCGACCTCAA AAGAGTTGTG CTTGATGGTT CCGTGGCAAC CCCTATAACC   600

AGAGTTTCAG CGGAACAATG GGGTCGTCCT TAGATGACTT CTGTCATGAT AGCACGGCTC   660

CAGAAAAGGT GCTTTTGGCG TTTTCTATTA CCTACACGCC AGTGATGATA TATGCC       716
```